United States Patent [19]
Kong et al.

[11] Patent Number: 5,814,506
[45] Date of Patent: Sep. 29, 1998

[54] OVER-EXPRESSION AND PURIFICATION OF A TRUNCATED THERMOSTABLE DNA POLYMERASE BY PROTEIN FUSION

[75] Inventors: Huimin Kong, Wenham; John J. Pelletier, Amesbury; Jason M. Aliotta, Newton, all of Mass.

[73] Assignee: New England Biolabs, Inc., Beverly, Mass.

[21] Appl. No.: 510,215

[22] Filed: Aug. 2, 1995

[51] Int. Cl.[6] .............................. C12N 9/12; C12N 15/54; C12N 15/62
[52] U.S. Cl. .................. 435/194; 435/320.1; 435/252.3; 435/325; 435/419; 536/23.2; 536/23.4
[58] Field of Search ................... 435/194, 320.1, 435/252.3, 325, 419; 536/23.2, 23.4

[56] References Cited

U.S. PATENT DOCUMENTS

| | | | |
|---|---|---|---|
| 4,683,195 | 7/1987 | Mullis et al. | 435/194 |
| 4,683,202 | 7/1987 | Mullis | 435/194 |
| 4,800,159 | 1/1989 | Mullis et al. | 435/194 |

FOREIGN PATENT DOCUMENTS

| | | |
|---|---|---|
| 0 416 755 | 3/1991 | European Pat. Off. . |
| 0 517 418 A2 | 5/1992 | European Pat. Off. . |
| 0 699 760 | 4/1995 | European Pat. Off. . |
| 0 712 927 | 11/1995 | European Pat. Off. . |
| WO 94/16107 | 1/1994 | WIPO . |
| WO 95/27067 | 3/1995 | WIPO . |

OTHER PUBLICATIONS

Database WPI Section CH, Week 9351; Derwent Publications Ltd., London, GB; Class B04, AN 93–408323; XP002019902 (Nov. 19, 1993).
Uemori, et al., J. Biochem., 1133(3):401–410 (1993).
Bernad, et al., Cell, 59:219–228 (1989).
New England Biolabs Catalog 1993/94, Beverly, Massachusetts, USA p. 116 XP002019907 "Protein Fusion And Purification System" Abstract.
Aliotta, et al., Genet. Anal.:Biomol. Eng. 12:185–196 (1996).
Kong, et al., J. Biol. Chem. 268:1965–1975 (1993).
Stenesh and Roe, Biochim. Biophys. Acta, 272:156–6 (1972).
Kaboev, et al., J. Bacteriol., 145:21–26 (1981).
Sellmann, et al., J. Bacteriol., 174:4350–4355 (1992).
Lawyer, et al., J. Biol. Chem., 264:6427–6437 (1989).
Ye, Scientia Sinica, 30:503–506 (1987).
McClary, DNA SEQ, 1:173–180 (1991).
Walker, et al., Proc. Natl. Acad. Sci. USA, 89:392–396 (1992).
Guan, et al., Gene, 67:21–30 (1987).
Maina, et al., Gene, 74:365–373 (1988).
Kellerman and Ferenci, Methods in Enzymol., 90:459–463 (1982).
Matsudaira, et al., J. Biol. Chem., 262:10035–10038 (1987).
Waite–Rees, et al., J. Bacteriol., 173:5207–5219 (1991).
GenBank Accession No. U23149 Sequence Listing.
GenBank Accession No. L42111 Sequence Listing.

*Primary Examiner*—Keith D. Hendricks
*Attorney, Agent, or Firm*—Gregory D. Williams

[57] ABSTRACT

The present invention relates to the cloning and purification of a thermostable DNA polymerase, Bst polymerase I from *Bacillus stearothermophilus*. More specifically, it provides a novel method for producing a truncated Bst polymerase using recombinant DNA and protein fusion techniques.

15 Claims, 6 Drawing Sheets

```
ATGAAGAAGAAGCTAGTACTAATTGATGGCAACAGTGTGGCATACCGCGCCTTTTTTGCCTTGCCACTTTTGCATAACGACAAAGGCATT
 M  K  K  K  L  V  L  I  D  G  N  S  V  A  Y  R  A  F  F  A  L  P  L  L  H  N  D  K  G  I

CATACGAATGCGGTTTACGGGTTTACGATGATGTTGAACAAATTTGGCGGAAGAACACCGACCCATTACTTGTAGCGTTTGACGCC
 H  T  N  A  V  Y  G  F  T  M  M  L  N  K  I  L  A  E  E  Q  P  T  H  L  L  V  A  F  D  A

GGAAAAACGACGTTCCGGCATGAAACGTTTCAAGAGTATAAAGGCGACGGCAACAAACTCCCCGGAACTGTCCGAGCAGTTTCCGCTG
 G  K  T  F  R  H  E  T  F  Q  E  Y  K  G  G  R  Q  Q  T  P  P  E  L  S  E  Q  F  P  L

TTGCGCGAGCTATTAAAAGCGTACCGCATTCCCGCTTATGAACTTGATCATTACGAAGCGGACGATATTATCGGGACGCTCGCCCGC
 L  R  E  L  L  K  A  Y  R  I  P  A  Y  E  L  D  H  Y  E  A  D  D  I  I  G  T  L  A  A  R

GCTGAGCAAGAAGGGTTTGAAGTCAAGATCATTTCCGGCGACCGCGATTTAACCCAGCTCCCCGTCATGTGACGGTCGATATTACG
 A  E  Q  E  G  F  E  V  K  I  I  S  G  D  R  D  L  T  Q  L  A  S  R  H  V  T  V  D  I  T

AAAAAAGGGATTACCGACATTGAGCCGTATACGCCAGAGACCGTTCGCGAAAATACGGCCGTTAAAGCTGTCAAGCTGAAATTGGTACG
 K  K  G  I  T  D  I  E  P  Y  T  P  E  T  V  R  E  K  Y  G  L  T  P  E  Q  I  V  D  L  K

GGATTGATGGGCGATAAATCCGACAACATCCCGGGCGTGCCCGGCATCGGGGAAAAGGGGAAAGAAACTGAAAGAAAACTGCGCCAACACCGGATTTAGCTCTCTTGAGC
 G  L  M  G  D  K  S  D  N  I  P  G  V  P  G  I  G  E  K  T  A  V  K  L  L  K  Q  F  G  T

GTGGAAAATGTGCTCGCATCGATTGATGAGGTGAAAGGGGAGAAGCTGAAAGAAAACTTGCGCCAACACCGGATTTAGCTCTCTTGAGC
 V  E  N  V  L  A  S  I  D  E  V  K  G  E  K  L  K  E  N  L  R  Q  H  R  D  L  A  L  L  S

AAACAGCTGGCCGTCCATTGCCGCGACGCCCCGGTTGAGCTGTCTTAGATGACATTGTCTACGAAGGACAAGACCGGCGAAAAAGTCATC
 K  Q  L  A  S  I  C  R  D  A  P  V  E  L  S  L  D  D  I  V  Y  E  G  Q  D  R  E  K  V  I
```

FIG. 2A

GCGTTATTAAAGAACTCGGGTTTCAGTCGTTCTTGGAAAAAATGGCCCGCCGCCAAGGGGAGAAACCGCTTGAGGAGATGGAG
A  L  F  K  E  L  G  F  Q  S  F  L  E  K  M  A  A  P  A  *A  E  G  E  K  P  L  E  E  M  E

TTTGCCATCGTTGACGTCATTACCGAAGAGATGCTTGCCGACAAGGCAGCGCTTGTCGTTGAGGTGATGGAAGAAAACTACCACGATGCC
F  A  I  V  D  V  I  T  E  E  M  L  A  D  K  A  A  L  V  V  E  V  M  E  E  N  Y  H  D  A

CCGATTGTCGGAATCGCACTAGTGAACGAGCATGGGCGCGATTTTTATGCGCCCGAGACCGCGCTGGCTGATTCGCAATTTTTAGCATGG
P  I  V  G  I  A  L  V  N  E  H  G  R  F  F  M  R  P  E  T  A  L  A  D  S  Q  F  L  A  W

CTTGCCGATGAAACGAAGAAAAAGCATGTTGACGCCAAGCGCGCAGTCGTTGCCTTAAAGTGGAAAGGAATTGAGCTTCGCGGCGTC
L  A  D  E  T  K  K  K  S  M  F  D  A  K  R  A  V  V  A  L  K  W  K  G  I  E  L  R  G  V

GCCTTTGATTTATTGCTCGCTGCCTATTGCTCAATCCGGCTCAAGATGCCGGCGTGGCCGAAATGAAACAATATGAA
A  F  D  L  L  L  A  A  Y  L  L  N  P  A  Q  D  A  G  D  I  A  A  V  A  K  M  K  Q  Y  E

GCGGTGCGGTCGGATGAAGCGGTCTATGGCAAAGGCGTCAAGCGCCTTGCTGAGCATCTCGTTCGCAAA
A  V  R  S  D  E  A  V  Y  G  K  G  V  K  R  S  L  P  D  E  Q  T  L  A  E  H  L  V  R  K

GCGGCAGCCATTTGGGCGCTTGAGCAGCCGTTTATGGACGATTTGCGGAACAACGAACAAGATCAATTATTAACGAAGCTTGAGCAGCCG
A  A  A  I  W  A  L  E  Q  P  F  M  D  D  L  R  N  N  E  Q  D  Q  L  L  T  K  L  E  Q  P

CTGCGGGCGATTTTGGCTGAAATGGAATTCACTGGGGTGAATGTGGATACAAAGCGGCTTGAACAGATGGGTTCGGAGCTCGCCGAACAA
L  A  A  I  L  A  E  M  E  F  T  G  V  N  V  D  T  K  R  L  E  Q  M  G  S  E  L  A  E  Q

CTGCGTGCCATCGAGCAGCGCATTTACGAGCTAGCCGGCCAAGAAAACAGCTCTATTCGACTTCGACTTGAGAAGCTTGCTGATGTGCTTGAGTCTCGGAGTCATTTTATTGAA
L  R  A  I  E  Q  R  I  Y  E  L  A  G  Q  E  F  N  I  N  S  P  K  Q  L  G  V  I  L  F  E

AAGCTGCAGCTACCGGTGCTGAAGAAGACGAAAACAGGCTATATTCGGTGCTTGAGAAGCTTGCCGCCGCCATCATGAAATC
K  L  Q  L  P  V  L  K  K  T  K  T  G  Y  S  T  S  A  D  V  L  E  K  L  A  P  H  H  E  I

GTCGAAAACATTTGCATTACGCCAGCTTGGCAAACTGCAATCAACGTATATTGAAGGATTGTTGAAAGTTGTGCGCCCTGATACCGGC
V  E  N  I  L  H  Y  R  Q  L  G  K  L  Q  S  T  Y  I  E  G  L  L  K  V  V  R  P  D  T  G

FIG. 2B

AAAGTGCATACGATGTTCAACCAAGCGCTGACGCAAACTGGGCGGCTCGACTCGGCCGAGCCAAACTTGCAAAACATTCCGATTCGGCTC
 K  V  H  T  M  F  N  Q  A  L  T  Q  T  G  R  L  S  S  A  E  P  N  L  Q  N  I  P  I  R  L

GAAGAGGGGCGAAAATCCGCCAAGCGTTCGTCCCGTCAGAGCCGATTACTCATTTCGCCGCCGATTACTCACAAATTGAATTGCGC
 E  E  G  R  K  I  R  Q  A  F  V  P  S  E  P  D  W  L  I  F  A  A  D  Y  S  Q  I  E  L  R

GTCCTCGCCCATATCGCCGATGACGACAATCTAATTGAAGCGTTCCAACGCGATTTGGATATTCACACAAAAACGGCGATGGACATTTC
 V  L  A  H  I  A  D  D  D  N  L  I  E  A  F  Q  R  D  L  D  I  H  T  K  T  A  M  D  I  F

CATGTGAGCGAAGAGGAAGTCACGGCCAACATGCGCCGCCAGGCAAAGGCCGTTAACTTCGTTACGGAATTAGCGATTACGGA
 H  V  S  E  E  E  V  T  A  N  M  R  R  Q  A  K  A  V  N  F  G  I  V  Y  G  I  S  D  Y  G

TTGGGCAAAACTTGTGCAAGAAGCTGCCGAATTTATCGAACGTTACTTCGCCAGCTTTCCGGGCGTAAAGCAGTATATG
 L  A  Q  N  L  N  I  T  R  K  E  A  A  E  F  I  E  R  Y  F  A  S  F  P  G  V  K  Q  Y  M

GAAAACATTGTGCAAGAAGCGAAACAGAAGGGATATGTGACAACGCTGTTGCATCGGCGCTATTTGCCTGATATTACAAGCCGCAAT
 E  N  I  V  Q  E  A  K  Q  K  G  Y  V  T  T  L  L  H  R  R  Y  L  P  D  I  T  S  R  N

TTCAACGTCCGCAGTTTTGCAGAGAGAACAGCGGCCATGAACACGCCATTCAAGGAAGCGCCGCCAATTCAAGGAAGCGCCGCTGACATTATTAAAAAGCGATGATTGAT
 F  N  V  R  S  F  A  E  R  T  A  M  N  T  P  I  Q  G  S  A  A  D  I  I  K  K  A  M  I  D

TTAGCGGCACGGCTGAAAGAAGAGCAGCTTCAGGCTCGTCTTTTGCTGCAAGTGCATGACGAGCTCATTTTGGAAGCCAAAGAGGAA
 L  A  R  L  K  E  E  Q  L  Q  A  R  L  L  L  Q  V  H  D  E  L  I  L  E  A  P  K  E  E

ATTGAGGCGATTATGTGAGCTTGTTCCGGAAGTGATGGAGCAGGCCGTTACGCTGCGCCTGAAAGTCGACTACTATTACGGCCCA
 I  E  R  L  C  E  L  V  P  E  V  M  E  Q  A  V  T  L  R  V  P  L  K  V  D  Y  H  Y  G  P

ACATGGTATGATGCCAAATAA
 T  W  Y  D  A  K  *

FIG. 2C

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 2631 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..2631

( x i ) SEQUENCE DESCRIPTION: SEQ ID NO:1:

```
ATG  AAG  AAG  AAG  CTA  GTA  CTA  ATT  GAT  GGC  AAC  AGT  GTG  GCA  TAC  CGC       48
Met  Lys  Lys  Lys  Leu  Val  Leu  Ile  Asp  Gly  Asn  Ser  Val  Ala  Tyr  Arg
 1              5                        10                       15

GCC  TTT  TTT  GCC  TTG  CCA  CTT  TTG  CAT  AAC  GAC  AAA  GGC  ATT  CAT  ACG       96
Ala  Phe  Phe  Ala  Leu  Pro  Leu  Leu  His  Asn  Asp  Lys  Gly  Ile  His  Thr
               20                       25                       30

AAT  GCG  GTT  TAC  GGG  TTT  ACG  ATG  ATG  TTG  AAC  AAA  ATT  TTG  GCG  GAA      144
Asn  Ala  Val  Tyr  Gly  Phe  Thr  Met  Met  Leu  Asn  Lys  Ile  Leu  Ala  Glu
                    35                       40                       45

GAA  CAA  CCG  ACC  CAT  TTA  CTT  GTA  GCG  TTT  GAC  GCC  GGA  AAA  ACG  ACG      192
Glu  Gln  Pro  Thr  His  Leu  Leu  Val  Ala  Phe  Asp  Ala  Gly  Lys  Thr  Thr
         50                       55                       60

TTC  CGG  CAT  GAA  ACG  TTT  CAA  GAG  TAT  AAA  GGC  GGA  CGG  CAA  CAA  ACT      240
Phe  Arg  His  Glu  Thr  Phe  Gln  Glu  Tyr  Lys  Gly  Gly  Arg  Gln  Gln  Thr
 65                       70                       75                       80

CCC  CCG  GAA  CTG  TCC  GAG  CAG  TTT  CCG  CTG  TTG  CGC  GAG  CTA  TTA  AAA      288
Pro  Pro  Glu  Leu  Ser  Glu  Gln  Phe  Pro  Leu  Leu  Arg  Glu  Leu  Leu  Lys
                    85                       90                       95
```

| | | | | | | | | | | | | | | | | |
|---|---|---|---|---|---|---|---|---|---|---|---|---|---|---|---|---|
| GCG | TAC | CGC | ATT | CCC | GCT | TAT | GAA | CTT | GAT | CAT | TAC | GAA | GCG | GAC | GAT | 336 |
| Ala | Tyr | Arg | Ile 100 | Pro | Ala | Tyr | Glu 105 | Leu | Asp | His | Tyr | Glu 110 | Ala | Asp | Asp | |
| ATT | ATC | GGG | ACG | CTC | GCT | GCC | CGC | GCT | GAG | CAA | GAA | GGG | TTT | GAA | GTG | 384 |
| Ile | Ile | Gly 115 | Thr | Leu | Ala | Ala | Arg 120 | Ala | Glu | Gln | Glu | Gly 125 | Phe | Glu | Val | |
| AAA | ATC | ATT | TCC | GGC | GAC | CGC | GAT | TTA | ACC | CAG | CTC | GCC | TCC | CGT | CAT | 432 |
| Lys | Ile 130 | Ile | Ser | Gly | Asp | Arg 135 | Asp | Leu | Thr | Gln | Leu 140 | Ala | Ser | Arg | His | |
| GTG | ACG | GTC | GAT | ATT | ACG | AAA | AAA | GGG | ATT | ACC | GAC | ATT | GAG | CCG | TAT | 480 |
| Val 145 | Thr | Val | Asp | Ile | Thr 150 | Lys | Lys | Gly | Ile | Thr 155 | Asp | Ile | Glu | Pro | Tyr 160 | |
| ACG | CCA | GAG | ACC | GTT | CGC | GAA | AAA | TAC | GGC | CTG | ACT | CCG | GAG | CAA | ATA | 528 |
| Thr | Pro | Glu | Thr | Val 165 | Arg | Glu | Lys | Tyr | Gly 170 | Leu | Thr | Pro | Glu | Gln 175 | Ile | |
| GTG | GAT | TTA | AAA | GGA | TTG | ATG | GGC | GAT | AAA | TCC | GAC | AAC | ATC | CCG | GGC | 576 |
| Val | Asp | Leu | Lys 180 | Gly | Leu | Met | Gly | Asp 185 | Lys | Ser | Asp | Asn | Ile 190 | Pro | Gly | |
| GTG | CCC | GGC | ATC | GGG | GAA | AAA | ACG | GCG | GTC | AAG | CTG | CTG | AAG | CAA | TTT | 624 |
| Val | Pro | Gly 195 | Ile | Gly | Glu | Lys | Thr 200 | Ala | Val | Lys | Leu | Leu 205 | Lys | Gln | Phe | |
| GGT | ACG | GTG | GAA | AAT | GTG | CTC | GCA | TCG | ATT | GAT | GAG | GTG | AAA | GGG | GAA | 672 |
| Gly | Thr 210 | Val | Glu | Asn | Val | Leu 215 | Ala | Ser | Ile | Asp | Glu 220 | Val | Lys | Gly | Glu | |
| AAA | CTG | AAA | GAA | AAC | TTG | CGC | CAA | CAC | CGG | GAT | TTA | GCT | CTC | TTG | AGC | 720 |
| Lys 225 | Leu | Lys | Glu | Asn | Leu 230 | Arg | Gln | His | Arg | Asp 235 | Leu | Ala | Leu | Leu | Ser 240 | |
| AAA | CAG | CTG | GCG | TCC | ATT | TGC | CGC | GAC | GCC | CCG | GTT | GAG | CTG | TCG | TTA | 768 |
| Lys | Gln | Leu | Ala | Ser 245 | Ile | Cys | Arg | Asp | Ala 250 | Pro | Val | Glu | Leu | Ser 255 | Leu | |
| GAT | GAC | ATT | GTC | TAC | GAA | GGA | CAA | GAC | CGC | GAA | AAA | GTC | ATC | GCG | TTA | 816 |
| Asp | Asp | Ile | Val 260 | Tyr | Glu | Gly | Gln | Asp 265 | Arg | Glu | Lys | Val | Ile 270 | Ala | Leu | |
| TTT | AAA | GAA | CTC | GGG | TTT | CAG | TCG | TTC | TTG | GAA | AAA | ATG | GCC | GCG | CCG | 864 |
| Phe | Lys | Glu 275 | Leu | Gly | Phe | Gln | Ser 280 | Phe | Leu | Glu | Lys | Met 285 | Ala | Ala | Pro | |
| GCA | GCC | GAA | GGG | GAG | AAA | CCG | CTT | GAG | GAG | ATG | GAG | TTT | GCC | ATC | GTT | 912 |
| Ala | Ala 290 | Glu | Gly | Glu | Lys | Pro 295 | Leu | Glu | Glu | Met | Glu 300 | Phe | Ala | Ile | Val | |
| GAC | GTC | ATT | ACC | GAA | GAG | ATG | CTT | GCC | GAC | AAG | GCA | GCG | CTT | GTC | GTT | 960 |
| Asp 305 | Val | Ile | Thr | Glu | Glu 310 | Met | Leu | Ala | Asp | Lys 315 | Ala | Ala | Leu | Val | Val 320 | |
| GAG | GTG | ATG | GAA | GAA | AAC | TAC | CAC | GAT | GCC | CCG | ATT | GTC | GGA | ATC | GCA | 1008 |
| Glu | Val | Met | Glu | Glu 325 | Asn | Tyr | His | Asp | Ala 330 | Pro | Ile | Val | Gly | Ile 335 | Ala | |
| CTA | GTG | AAC | GAG | CAT | GGG | CGA | TTT | TTT | ATG | CGC | CCG | GAG | ACC | GCG | CTG | 1056 |
| Leu | Val | Asn | Glu 340 | His | Gly | Arg | Phe | Phe 345 | Met | Arg | Pro | Glu | Thr 350 | Ala | Leu | |
| GCT | GAT | TCG | CAA | TTT | TTA | GCA | TGG | CTT | GCC | GAT | GAA | ACG | AAG | AAA | AAA | 1104 |
| Ala | Asp | Ser 355 | Gln | Phe | Leu | Ala | Trp 360 | Leu | Ala | Asp | Glu | Thr 365 | Lys | Lys | Lys | |
| AGC | ATG | TTT | GAC | GCC | AAG | CGG | GCA | GTC | GTT | GCC | TTA | AAG | TGG | AAA | GGA | 1152 |
| Ser | Met | Phe 370 | Asp | Ala | Lys | Arg | Ala 375 | Val | Val | Ala | Leu | Lys 380 | Trp | Lys | Gly | |
| ATT | GAG | CTT | CGC | GGC | GTC | GCC | TTT | GAT | TTA | TTG | CTC | GCT | GCC | TAT | TTG | 1200 |
| Ile | Glu | Leu | Arg 385 | Gly | Val | Ala | Phe | Asp 390 | Leu | Leu | Leu | Ala | Ala 395 | Tyr | Leu 400 | |
| CTC | AAT | CCG | GCT | CAA | GAT | GCC | GGC | GAT | ATC | GCT | GCG | GTG | GCG | AAA | ATG | 1248 |
| Leu | Asn | Pro | Ala | Gln 405 | Asp | Ala | Gly | Asp | Ile 410 | Ala | Ala | Val | Ala | Lys 415 | Met | |

| | | | | | | | | | | | | | | | | |
|---|---|---|---|---|---|---|---|---|---|---|---|---|---|---|---|---|
| AAA | CAA | TAT | GAA | GCG | GTG | CGG | TCG | GAT | GAA | GCG | GTC | TAT | GGC | AAA | GGC | 1296 |
| Lys | Gln | Tyr | Glu 420 | Ala | Val | Arg | Ser | Asp 425 | Glu | Ala | Val | Tyr | Gly 430 | Lys | Gly | |
| GTC | AAG | CGG | TCG | CTG | CCG | GAC | GAA | CAG | ACG | CTT | GCT | GAG | CAT | CTC | GTT | 1344 |
| Val | Lys | Arg 435 | Ser | Leu | Pro | Asp | Glu | Thr 440 | Leu | Ala | Glu | His 445 | Leu | Val | | |
| CGC | AAA | GCG | GCA | GCC | ATT | TGG | GCG | CTT | GAG | CAG | CCG | TTT | ATG | GAC | GAT | 1392 |
| Arg | Lys 450 | Ala | Ala | Ala | Ile | Trp 455 | Ala | Leu | Glu | Gln | Pro 460 | Phe | Met | Asp | Asp | |
| TTG | CGG | AAC | AAC | GAA | CAA | GAT | CAA | TTA | TTA | ACG | AAG | CTT | GAG | CAG | CCG | 1440 |
| Leu 465 | Arg | Asn | Asn | Glu | Gln 470 | Asp | Gln | Leu | Leu | Thr 475 | Lys | Leu | Glu | Gln | Pro 480 | |
| CTG | GCG | GCG | ATT | TTG | GCT | GAA | ATG | GAA | TTC | ACT | GGG | GTG | AAC | GTG | GAT | 1488 |
| Leu | Ala | Ala | Ile | Leu 485 | Ala | Glu | Met | Glu | Phe 490 | Thr | Gly | Val | Asn | Val 495 | Asp | |
| ACA | AAG | CGG | CTT | GAA | CAG | ATG | GGT | TCG | GAG | CTC | GCC | GAA | CAA | CTG | CGT | 1536 |
| Thr | Lys | Arg | Leu 500 | Glu | Gln | Met | Gly | Ser 505 | Glu | Leu | Ala | Glu | Gln 510 | Leu | Arg | |
| GCC | ATC | GAG | CAG | CGC | ATT | TAC | GAG | CTA | GCC | GGC | CAA | GAG | TTC | AAC | ATT | 1584 |
| Ala | Ile | Glu 515 | Gln | Arg | Ile | Tyr | Glu 520 | Leu | Ala | Gly | Gln | Glu 525 | Phe | Asn | Ile | |
| AAC | TCA | CCA | AAA | CAG | CTC | GGA | GTC | ATT | TTA | TTT | GAA | AAG | CTG | CAG | CTA | 1632 |
| Asn | Ser 530 | Pro | Lys | Gln | Leu | Gly 535 | Val | Ile | Leu | Phe | Glu 540 | Lys | Leu | Gln | Leu | |
| CCG | GTG | CTG | AAG | AAG | ACG | AAA | ACA | GGC | TAT | TCG | ACT | TCG | GCT | GAT | GTG | 1680 |
| Pro 545 | Val | Leu | Lys | Lys | Thr 550 | Lys | Thr | Gly | Tyr | Ser 555 | Thr | Ser | Ala | Asp | Val 560 | |
| CTT | GAG | AAG | CTT | GCG | CCG | CAT | CAT | GAA | ATC | GTC | GAA | AAC | ATT | TTG | CAT | 1728 |
| Leu | Glu | Lys | Leu | Ala 565 | Pro | His | His | Glu | Ile 570 | Val | Glu | Asn | Ile | Leu 575 | His | |
| TAC | CGC | CAG | CTT | GGC | AAA | CTG | CAA | TCA | ACG | TAT | ATT | GAA | GGA | TTG | TTG | 1776 |
| Tyr | Arg | Gln | Leu 580 | Gly | Lys | Leu | Gln | Ser 585 | Thr | Tyr | Ile | Glu | Gly 590 | Leu | Leu | |
| AAA | GTT | GTG | CGC | CCT | GAT | ACC | GGC | AAA | GTG | CAT | ACG | ATG | TTC | AAC | CAA | 1824 |
| Lys | Val | Val 595 | Arg | Pro | Asp | Thr | Gly 600 | Lys | Val | His | Thr | Met 605 | Phe | Asn | Gln | |
| GCG | CTG | ACG | CAA | ACT | GGG | CGG | CTC | AGC | TCG | GCC | GAG | CCG | AAC | TTG | CAA | 1872 |
| Ala | Leu 610 | Thr | Gln | Thr | Gly | Arg 615 | Leu | Ser | Ser | Ala | Glu 620 | Pro | Asn | Leu | Gln | |
| AAC | ATT | CCG | ATT | CGG | CTC | GAA | GAG | GGG | CGG | AAA | ATC | CGC | CAA | GCG | TTC | 1920 |
| Asn | Ile 625 | Pro | Ile | Arg | Leu 630 | Glu | Glu | Gly | Arg | Lys 635 | Ile | Arg | Gln | Ala | Phe 640 | |
| GTC | CCG | TCA | GAG | CCG | GAC | TGG | CTC | ATT | TTC | GCC | GCC | GAT | TAC | TCA | CAA | 1968 |
| Val | Pro | Ser | Glu | Pro 645 | Asp | Trp | Leu | Ile | Phe 650 | Ala | Ala | Asp | Tyr | Ser 655 | Gln | |
| ATT | GAA | TTG | CGC | GTC | CTC | GCC | CAT | ATC | GCC | GAT | GAC | GAC | AAT | CTA | ATT | 2016 |
| Ile | Glu | Leu | Arg 660 | Val | Leu | Ala | His | Ile 665 | Ala | Asp | Asp | Asp | Asn 670 | Leu | Ile | |
| GAA | GCG | TTC | CAA | CGC | GAT | TTG | GAT | ATT | CAC | ACA | AAA | ACG | GCG | ATG | GAC | 2064 |
| Glu | Ala | Phe 675 | Gln | Arg | Asp | Leu | Asp 680 | Ile | His | Thr | Lys | Thr 685 | Ala | Met | Asp | |
| ATT | TTC | CAT | GTG | AGC | GAA | GAG | GAA | GTC | ACG | GCC | AAC | ATG | CGC | CGC | CAG | 2112 |
| Ile | Phe | His 690 | Val | Ser | Glu | Glu | Glu 695 | Val | Thr | Ala | Asn | Met 700 | Arg | Arg | Gln | |
| GCA | AAG | GCC | GTT | AAC | TTC | GGT | ATC | GTT | TAC | GGA | ATT | AGC | GAT | TAC | GGA | 2160 |
| Ala | Lys | Ala 705 | Val | Asn | Phe | Gly | Ile 710 | Val | Tyr | Gly | Ile | Ser 715 | Asp | Tyr | Gly 720 | |
| TTG | GCG | CAA | AAC | TTG | AAC | ATT | ACG | CGC | AAA | GAA | GCT | GCC | GAA | TTT | ATC | 2208 |
| Leu | Ala | Gln | Asn | Leu 725 | Asn | Ile | Thr | Arg | Lys 730 | Glu | Ala | Ala | Glu | Phe 735 | Ile | |

|   |   |   |   |   |   |   |   |   |   |   |   |   |   |   |   |      |
|---|---|---|---|---|---|---|---|---|---|---|---|---|---|---|---|------|
| GAA | CGT | TAC | TTC | GCC | AGC | TTT | CCG | GGC | GTA | AAG | CAG | TAT | ATG | GAA | AAC | 2256 |
| Glu | Arg | Tyr | Phe | Ala | Ser | Phe | Pro | Gly | Val | Lys | Gln | Tyr | Met | Glu | Asn |      |
|     | 740 |     |     |     |     |     | 745 |     |     |     |     | 750 |     |     |     |      |
| ATT | GTG | CAA | GAA | GCG | AAA | CAG | AAA | GGA | TAT | GTG | ACA | ACG | CTG | TTG | CAT | 2304 |
| Ile | Val | Gln | Glu | Ala | Lys | Gln | Lys | Gly | Tyr | Val | Thr | Thr | Leu | Leu | His |      |
|     |     | 755 |     |     |     |     | 760 |     |     |     |     | 765 |     |     |     |      |
| CGG | CGC | CGC | TAT | TTG | CCT | GAT | ATT | ACA | AGC | CGC | AAT | TTC | AAC | GTC | CGC | 2352 |
| Arg | Arg | Arg | Tyr | Leu | Pro | Asp | Ile | Thr | Ser | Arg | Asn | Phe | Asn | Val | Arg |      |
|     | 770 |     |     |     |     | 775 |     |     |     |     | 780 |     |     |     |     |      |
| AGT | TTT | GCA | GAG | CGG | ACG | GCC | ATG | AAC | ACG | CCA | ATT | CAA | GGA | AGC | GCC | 2400 |
| Ser | Phe | Ala | Glu | Arg | Thr | Ala | Met | Asn | Thr | Pro | Ile | Gln | Gly | Ser | Ala |      |
| 785 |     |     |     |     | 790 |     |     |     |     | 795 |     |     |     |     | 800 |      |
| GCT | GAC | ATT | ATT | AAA | AAA | GCG | ATG | ATT | GAT | TTA | GCG | GCA | CGG | CTG | AAA | 2448 |
| Ala | Asp | Ile | Ile | Lys | Lys | Ala | Met | Ile | Asp | Leu | Ala | Ala | Arg | Leu | Lys |      |
|     |     |     |     | 805 |     |     |     |     | 810 |     |     |     |     | 815 |     |      |
| GAA | GAG | CAG | CTT | CAG | GCT | CGT | CTT | TTG | CTG | CAA | GTG | CAT | GAC | GAG | CTC | 2496 |
| Glu | Glu | Gln | Leu | Gln | Ala | Arg | Leu | Leu | Leu | Gln | Val | His | Asp | Glu | Leu |      |
| 820 |     |     |     |     |     |     |     | 825 |     |     |     |     | 830 |     |     |      |
| ATT | TTG | GAA | GCG | CCA | AAA | GAG | GAA | ATT | GAG | CGA | TTA | TGT | GAG | CTT | GTT | 2544 |
| Ile | Leu | Glu | Ala | Pro | Lys | Glu | Glu | Ile | Glu | Arg | Leu | Cys | Glu | Leu | Val |      |
|     |     | 835 |     |     |     |     | 840 |     |     |     |     | 845 |     |     |     |      |
| CCG | GAA | GTG | ATG | GAG | CAG | GCC | GTT | ACG | CTC | CGC | GTG | CCG | CTG | AAA | GTC | 2592 |
| Pro | Glu | Val | Met | Glu | Gln | Ala | Val | Thr | Leu | Arg | Val | Pro | Leu | Lys | Val |      |
|     | 850 |     |     |     |     | 855 |     |     |     |     | 860 |     |     |     |     |      |
| GAC | TAC | CAT | TAC | GGC | CCA | ACA | TGG | TAT | GAT | GCC | AAA | TAA |     |     |     | 2631 |
| Asp | Tyr | His | Tyr | Gly | Pro | Thr | Trp | Tyr | Asp | Ala | Lys |     |     |     |     |      |
| 865 |     |     |     |     | 870 |     |     |     |     | 875 |     |     |     |     |     |      |

(2) INFORMATION FOR SEQ ID NO:2:

(i) SEQUENCE CHARACTERISTICS:
        (A) LENGTH: 876 amino acids
        (B) TYPE: amino acid
        (D) TOPOLOGY: linear (ii) MOLECULE TYPE: protein (xi) SEQUENCE DESCRIPTION: SEQ ID NO:2:

| Met | Lys | Lys | Lys | Leu | Val | Leu | Ile | Asp | Gly | Asn | Ser | Val | Ala | Tyr | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Phe | Phe | Ala | Leu | Pro | Leu | Leu | His | Asn | Asp | Lys | Gly | Ile | His | Thr |
|     |     |     | 20  |     |     |     |     | 25  |     |     |     |     | 30  |     |     |
| Asn | Ala | Val | Tyr | Gly | Phe | Thr | Met | Met | Leu | Asn | Lys | Ile | Leu | Ala | Glu |
|     |     | 35  |     |     |     |     | 40  |     |     |     |     | 45  |     |     |     |
| Glu | Gln | Pro | Thr | His | Leu | Leu | Val | Ala | Phe | Asp | Ala | Gly | Lys | Thr | Thr |
|     | 50  |     |     |     |     | 55  |     |     |     |     | 60  |     |     |     |     |
| Phe | Arg | His | Glu | Thr | Phe | Gln | Glu | Tyr | Lys | Gly | Gly | Arg | Gln | Gln | Thr |
| 65  |     |     |     |     | 70  |     |     |     |     | 75  |     |     |     |     | 80  |
| Pro | Pro | Glu | Leu | Ser | Glu | Gln | Phe | Pro | Leu | Leu | Arg | Glu | Leu | Leu | Lys |
|     |     |     |     | 85  |     |     |     |     | 90  |     |     |     |     | 95  |     |
| Ala | Tyr | Arg | Ile | Pro | Ala | Tyr | Glu | Leu | Asp | His | Tyr | Glu | Ala | Asp | Asp |
|     |     |     | 100 |     |     |     |     | 105 |     |     |     |     | 110 |     |     |
| Ile | Ile | Gly | Thr | Leu | Ala | Ala | Arg | Ala | Glu | Gln | Glu | Gly | Phe | Glu | Val |
|     |     | 115 |     |     |     |     | 120 |     |     |     |     | 125 |     |     |     |
| Lys | Ile | Ile | Ser | Gly | Asp | Arg | Asp | Leu | Thr | Gln | Leu | Ala | Ser | Arg | His |
|     | 130 |     |     |     |     | 135 |     |     |     |     | 140 |     |     |     |     |
| Val | Thr | Val | Asp | Ile | Thr | Lys | Lys | Gly | Ile | Thr | Asp | Ile | Glu | Pro | Tyr |
| 145 |     |     |     |     | 150 |     |     |     |     | 155 |     |     |     |     | 160 |
| Thr | Pro | Glu | Thr | Val | Arg | Glu | Lys | Tyr | Gly | Leu | Thr | Pro | Glu | Gln | Ile |
|     |     |     |     | 165 |     |     |     |     | 170 |     |     |     |     | 175 |     |

| | | | | | | | | | | | | | | |
|---|---|---|---|---|---|---|---|---|---|---|---|---|---|---|
|Val|Asp|Leu|Lys|Gly|Leu|Met|Gly|Asp|Lys|Ser|Asp|Asn|Ile|Pro|Gly|
| | | |180| | | |185| | | |190| | | |
|Val|Pro|Gly|Ile|Gly|Glu|Lys|Thr|Ala|Val|Lys|Leu|Leu|Lys|Gln|Phe|
| | |195| | | |200| | | |205| | | | |
|Gly|Thr|Val|Glu|Asn|Val|Leu|Ala|Ser|Ile|Asp|Glu|Val|Lys|Gly|Glu|
| |210| | | |215| | | |220| | | | | |
|Lys|Leu|Lys|Glu|Asn|Leu|Arg|Gln|His|Arg|Asp|Leu|Ala|Leu|Leu|Ser|
|225| | | |230| | | |235| | | | | | |240|
|Lys|Gln|Leu|Ala|Ser|Ile|Cys|Arg|Asp|Ala|Pro|Val|Glu|Leu|Ser|Leu|
| | | |245| | | |250| | | |255| | | |
|Asp|Asp|Ile|Val|Tyr|Glu|Gly|Gln|Asp|Arg|Glu|Lys|Val|Ile|Ala|Leu|
| | |260| | | |265| | | |270| | | | |
|Phe|Lys|Glu|Leu|Gly|Phe|Gln|Ser|Phe|Leu|Glu|Lys|Met|Ala|Ala|Pro|
| |275| | | |280| | | |285| | | | | |
|Ala|Ala|Glu|Gly|Glu|Lys|Pro|Leu|Glu|Glu|Met|Glu|Phe|Ala|Ile|Val|
| |290| | | |295| | | |300| | | | | |
|Asp|Val|Ile|Thr|Glu|Glu|Met|Leu|Ala|Asp|Lys|Ala|Ala|Leu|Val|Val|
|305| | | |310| | | |315| | | | | | |320|
|Glu|Val|Met|Glu|Glu|Asn|Tyr|His|Asp|Ala|Pro|Ile|Val|Gly|Ile|Ala|
| | | |325| | | |330| | | |335| | | |
|Leu|Val|Asn|Glu|His|Gly|Arg|Phe|Phe|Met|Arg|Pro|Glu|Thr|Ala|Leu|
| | |340| | | |345| | | |350| | | | |
|Ala|Asp|Ser|Gln|Phe|Leu|Ala|Trp|Leu|Ala|Asp|Glu|Thr|Lys|Lys|Lys|
| |355| | | |360| | | |365| | | | | |
|Ser|Met|Phe|Asp|Ala|Lys|Arg|Ala|Val|Val|Ala|Leu|Lys|Trp|Lys|Gly|
| |370| | | |375| | | |380| | | | | |
|Ile|Glu|Leu|Arg|Gly|Val|Ala|Phe|Asp|Leu|Leu|Leu|Ala|Ala|Tyr|Leu|
|385| | | |390| | | |395| | | | | | |400|
|Leu|Asn|Pro|Ala|Gln|Asp|Ala|Gly|Asp|Ile|Ala|Ala|Val|Ala|Lys|Met|
| | | |405| | | |410| | | |415| | | |
|Lys|Gln|Tyr|Glu|Ala|Val|Arg|Ser|Asp|Glu|Ala|Val|Tyr|Gly|Lys|Gly|
| | |420| | | |425| | | |430| | | | |
|Val|Lys|Arg|Ser|Leu|Pro|Asp|Glu|Gln|Thr|Leu|Ala|Glu|His|Leu|Val|
| |435| | | |440| | | |445| | | | | |
|Arg|Lys|Ala|Ala|Ala|Ile|Trp|Ala|Leu|Glu|Gln|Pro|Phe|Met|Asp|Asp|
| |450| | | |455| | | |460| | | | | |
|Leu|Arg|Asn|Asn|Glu|Gln|Asp|Gln|Leu|Leu|Thr|Lys|Leu|Glu|Gln|Pro|
|465| | | |470| | | |475| | | | | | |480|
|Leu|Ala|Ala|Ile|Leu|Ala|Glu|Met|Glu|Phe|Thr|Gly|Val|Asn|Val|Asp|
| | | |485| | | |490| | | |495| | | |
|Thr|Lys|Arg|Leu|Glu|Gln|Met|Gly|Ser|Glu|Leu|Ala|Glu|Gln|Leu|Arg|
| | |500| | | |505| | | |510| | | | |
|Ala|Ile|Glu|Gln|Arg|Ile|Tyr|Glu|Leu|Ala|Gly|Gln|Glu|Phe|Asn|Ile|
| | |515| | | |520| | | |525| | | | |
|Asn|Ser|Pro|Lys|Gln|Leu|Gly|Val|Ile|Leu|Phe|Glu|Lys|Leu|Gln|Leu|
| |530| | | |535| | | |540| | | | | |
|Pro|Val|Leu|Lys|Lys|Thr|Lys|Thr|Gly|Tyr|Ser|Thr|Ser|Ala|Asp|Val|
|545| | | |550| | | |555| | | | | | |560|
|Leu|Glu|Lys|Leu|Ala|Pro|His|His|Glu|Ile|Val|Glu|Asn|Ile|Leu|His|
| | | |565| | | |570| | | |575| | | |
|Tyr|Arg|Gln|Leu|Gly|Lys|Leu|Gln|Ser|Thr|Tyr|Ile|Glu|Gly|Leu|Leu|
| | |580| | | |585| | | |590| | | | |
|Lys|Val|Val|Arg|Pro|Asp|Thr|Gly|Lys|Val|His|Thr|Met|Phe|Asn|Gln|

|  |  |  |  |  | 595 |  |  |  |  | 600 |  |  |  |  | 605 |  |
|---|---|---|---|---|---|---|---|---|---|---|---|---|---|---|---|---|

Ala Leu Thr Gln Thr Gly Arg Leu Ser Ser Ala Glu Pro Asn Leu Gln
610                         615                    620

Asn Ile Pro Ile Arg Leu Glu Glu Gly Arg Lys Ile Arg Gln Ala Phe
625                    630                    635                    640

Val Pro Ser Glu Pro Asp Trp Leu Ile Phe Ala Ala Asp Tyr Ser Gln
               645                    650                    655

Ile Glu Leu Arg Val Leu Ala His Ile Ala Asp Asp Asn Leu Ile
               660                    665                    670

Glu Ala Phe Gln Arg Asp Leu Asp Ile His Thr Lys Thr Ala Met Asp
          675                    680                    685

Ile Phe His Val Ser Glu Glu Val Thr Ala Asn Met Arg Arg Gln
     690                    695                    700

Ala Lys Ala Val Asn Phe Gly Ile Val Tyr Gly Ile Ser Asp Tyr Gly
705                    710                    715                    720

Leu Ala Gln Asn Leu Asn Ile Thr Arg Lys Glu Ala Ala Glu Phe Ile
                    725                    730                    735

Glu Arg Tyr Phe Ala Ser Phe Pro Gly Val Lys Gln Tyr Met Glu Asn
          740                    745                    750

Ile Val Gln Glu Ala Lys Gln Lys Gly Tyr Val Thr Thr Leu Leu His
          755                    760                    765

Arg Arg Arg Tyr Leu Pro Asp Ile Thr Ser Arg Asn Phe Asn Val Arg
770                    775                    780

Ser Phe Ala Glu Arg Thr Ala Met Asn Thr Pro Ile Gln Gly Ser Ala
785                    790                    795                    800

Ala Asp Ile Ile Lys Lys Ala Met Ile Asp Leu Ala Ala Arg Leu Lys
               805                    810                    815

Glu Glu Gln Leu Gln Ala Arg Leu Leu Leu Gln Val His Asp Glu Leu
          820                    825                    830

Ile Leu Glu Ala Pro Lys Glu Glu Ile Glu Arg Leu Cys Glu Leu Val
          835                    840                    845

Pro Glu Val Met Glu Gln Ala Val Thr Leu Arg Val Pro Leu Lys Val
     850                    855                    860

Asp Tyr His Tyr Gly Pro Thr Trp Tyr Asp Ala Lys
865                    870                    875

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:3:

Met Lys Lys Lys Leu Val Leu Ile Asp Gly Asn Ser Val Ala Tyr Arg
1                    5                    10                    15

Ala Phe Phe Ala Leu
               20

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown (ii) MOLECULE TYPE: protein (xi) SEQUENCE DESCRIPTION: SEQ ID NO:4:

Ala Glu Gly Glu Lys Pro Leu
1               5

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

GATTTAGCGG CACGGCTGAA AGAA 24

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

CTGCAAAACT GCGGACGTTG A 21

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:7:

Met Lys Lys Lys Leu Val Leu
1               5

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

WTGAARAARA ARCTNGTNYT 20

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

( x i ) SEQUENCE DESCRIPTION: SEQ ID NO:9:

TCTTATTTNG CATCATACCA TGT                                                                                      23

( 2 ) INFORMATION FOR SEQ ID NO:10:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:10:

TCCATGGCGG CCGCTCTTAT TTNGCATCAT ACCATGT                                                                       37

( 2 ) INFORMATION FOR SEQ ID NO:11:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:11:

ATTCTAGAGG AAACAGACCW TGAARAARAA CTNGTNYT                                                                      38

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:12:

Ala Glu Gly Glu Lys Pro Leu
    1               5

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:13:

AATTTGCGCA GAAGGGGAGA AACCGCTTGA                                                                               30

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:14:

TATTCTAGAT CTTATTTGGC ATCATACCAT GT                                                                            32

OVER-EXPRESSION AND PURIFICATION OF A TRUNCATED THERMOSTABLE DNA POLYMERASE BY PROTEIN FUSION

BACKGROUND OF THE INVENTION

DNA is the genetic material for most organisms. DNA polymerases are enzymes involved in DNA replication and repair.

Extensive research has been conducted on isolation and characterization of DNA polymerases from various organisms, including bacteria, yeast, and humans.

Besides the basic polymerization function, DNA polymerases may contain a 5'-3' or a 3'-5' exonuclease activity in the N-terminal domain of the polypeptide. If both exonucleases are present, the 5'-3' exonuclease domain is at the N-terminal followed by the 3'-5' exonuclease domain and the C-terminal polymerase domain. The 5'-3' exonuclease, excising DNA that lies in the path of the advancing DNA polymerase in a 5' to 3' direction, is required for nick-translation and repair. The 3'-5' exonuclease activity is required for proofreading by excising the mismatched nucleotide in a 3' to 5' direction. Three 3'-5' exonuclease motifs (Exo I, II, and III) have been identified by sequence comparisons (Blanco et al., (1991) Gene, 100, 27–38).

A number of thermostable DNA polymerases have been isolated from thermophilic eubacteria and thermophilic archaea. They can be divided into three groups based on their thermostabilities. DNA polymerases isolated from hyperthermophiles are stable at 100° C. For example, Vent®DNA polymerase from *Thermococcus litoralis* has a half-life of 2 hours at 100° C., which means that half of the polymerization activity of Vent polymerase will be retained after a 2 hour incubation at 100° C. (Kong, et al., *J. Biol. Chem.* 268: 1965–1975 (1993), the disclosure of which is hereby incorporated by reference herein). Isolated from an extreme thermophile, *Thermus aquaticus*, Taq DNA polymerase has a half-life of 1.6 hours at 95° C. (Kong, et al., *J. Biol. Chem.*, supra (1993), the disclosure of which is hereby incorporated by reference herein). Bst DNA polymerase I belongs to the third group, moderate thermophile, and is stable at 65° C.

Bst DNA polymerase was first isolated by Stenesh and Roe (Stenesh and Roe *Biochim. Biophys. Acta* 272: 156–6. (1972); Kaboev et al. *J. Bacteriol.,* 145:21–6 (1981), the disclosures of which are hereby incorporated by reference herein) further purified Bst DNA polymerase and concluded that it had a molecular mass of 76 kDa with both 5'-3' and 3'-5' exonuclease activities. The relative exonuclease to polymerase activities were very low, causing Kaboev to comment that they may be due to contamination. Sellman, et al., (Sellmann et al., *J. Bacteriol.,* 174: 4350–4355 (1992), the disclosure of which is hereby incorporated by reference herein) purified a 95 kDa Bst DNA polymerase with no exonuclease activity. Although Bst DNA polymerase seems to have been cloned (Epicentre Technology catalog), no publication regarding the cloning procedure and sequence information are available. Epicentre Technologies reports that both a 5'-3' and 3'-5' exonuclease activity are present in rBst DNA polymerase.

Thermophilic DNA polymerases are very useful in molecular biology and medical research. For example, The thermostable properties of the Taq DNA polymerase have contributed greatly to the yield, specificity, automation, and utility of the polymerase chain reaction method (U.S. Pat. Nos. 4,683,195; 4,683,202; and 4,800,159) for amplifying DNA (Lawyer, *J. Biol. Chem.,* 264: 6427–6437 (1989), the disclosure of which is hereby incorporated by reference herein). Another example is the use of the large fragment of Bst DNA polymerase (Bst L.F.) for DNA sequencing, (Ye, *Scientia Sinica,* 30: 503–506 (1987); McClary, DNA SEQ. 1: 173–180 (1991), the disclosures of which are hereby incorporated by reference herein). The thermostable Bst polymerase allows the sequencing reactions to be performed at high temperatures (65° C.) in order to melt secondary structure and results in uniform band intensities and low background on the autoradiogram. Bst L.F. can also be used in Strand Displacement Amplification (SDA), which is an isothermal exponential DNA amplification technique developed by G. Terrance Walker et al. at Becton Dickinson. See e.g. Walker et al., Proc. Natl.Acad.Sci. 89: 392–396 (1992), the disclosure of which is hereby incorporated by reference.

The N-terminal domain of Bst DNA polymerase is separable from the polymerization domain by a subtilisin (a proteinase) partial digestion, forming a 75 kDa DNA polymerase domain (termed the 'Large Fragment') analogous to the Klenow fragment of *E.coli* pol I (Ye, *Scientia Sinica,* supra (1987), the disclosure of which is hereby incorporated by reference herein). Although subtilisin can be used to generate the Bst L.F., the efficiency is low due to the non-specific degradation of Bst polymerase by the subtilisin. Accordingly, there is a need for novel methods of making BstI DNA polymerase, including the large fragment thereof, which overcome the disadvantages and inefficiencies of those previously produced.

SUMMARY OF THE INVENTION

The present invention relates to a thermophilic Bst DNA polymerase I as well as to methods of making a truncated thermophilic DNA polymerases in commercially useful amounts using recombinant DNA and protein fusion techniques.

More specifically, in one preferred embodiment there is provided a BstI DNA polymerase which differs from previously reported Bst polymerases in that it contains the 5'-3' exonuclease activity but not the 3'–5' exonuclease. In other preferred embodiments, the 5' to 3' exonuclease may also be rendered inactive. The present invention also provides a unique method to produce Bst DNA polymerase I large fragment using recombinant DNA and protein fusion techniques. In the protein fusion system, the cloned gene is inserted into a pMAL vector downstream from the malE gene, which encodes maltose-binding protein (MBP), resulting in the expression of an MBP-fusion protein (Guan, C et al. (1987) *Gene* 67, 21–30; Maina, C. V. et al. (1988) *gene* 74, 365–373), the disclosures of which are hereby incorporated by reference herein. This technique employs the strong Ptac promoter and the translation initiation signals of MBP to express large amount of the fusion protein. The fusion protein may then purified by one-step affinity purification for MBP (Kellerman and Ferenci (1982) *Methods in Enzumol.* 90, 459–463), the disclosure of which is hereby incorporated by reference herein.

In accordance with one preferred approach, The Bst DNA polymerase I of the present invention is purified from *Bacillus stearothermophilus* to near homogeneity and the sequence of its N-terminal first 21 amino acid residues was determined. A degenerated nucleotide oligo was made based on this amino acid sequence. To determine the 3' end nucleotide sequence of the Bst Pol I gene, inverse PCR was performed. Bst chromosomal DNA was digested with NgoM1 or Sau3Al and then ligated with T4 ligase to form a circle. The two primers that were used were designed using the sequence data of a 642-bp DNA fragment near the 3' end of the gene. This fragment was cloned based on the existence of the conserved amino acid sequence motifs in Pol I like DNA polymerases. The nucleotide sequence of the PCR fragments was determined and the 3' end of the Bst Pol I gene was identified. After both 5' end and 3' end nucleotide sequences were determined, the entire Bst Pol I gene was amplified by PCR and cloned it into pET21 a expression vector. Thermophilic Bst Pol I was made in E. coli containing the recombinant plasmid and the nucleotide sequence of the entire Bst Pol I gene was subsequently determined. Subtilisin partial digestions of Bst DNA polymerase were performed to make the large fragment of Bst Polymerase 1. Subtilisin partial digested fragment was made, and the N-terminal amino acid sequence of that large fragment was determined. Subsequent attempts to express the truncated gene in E. coli were unsuccessful. It is possible that the truncated mRNA or protein is unstable in vivo. It is also possible that the Bst large fragment is more lethal to the E. coli host than the holoenzyme and caused the cloning problem. To overcome the problems and also to simplify the purification steps, the 5'-end truncated Bst Pol I gene was cloned into the pMAL-c2 vector, hoping to stabilize the transcribed mRNA or make the translated protein more stable or less lethal by creating an MBP fusion protein. Indeed, the both fusion protein and cleaved Bst large fragment were active at 65° C.

BRIEF DESCRIPTION OF THE DRAWINGS

FIG. 2 is the nucleotide sequence (SEQ ID NO: 1) of Bst DNA polymerase I gene and its encoded protein sequence (SEQ ID NO: 2). The subtilisin cleavage site is indicated by "*" and the amino acid sequences, which were confirmed by N-terminal protein sequence, are shown in underline type.

Molecular weight markers in lanes M are: 212, 158, 116, 97.2, 66.4, 55.6, 42.7, 36.5, 26.6, 20.0, 14.3, and 6.5 kDa. The fusion protein corresponds to approximately 110 kDA. Factor Xa protease corresponds to approximately 39 kDa. The Bst Polymerase Large Fragment corresponds to approximately 67 kDa, and the MBP portion corresponds to approximately 42.7 kDa.

Figure 4:

FIG. 4 is a 10–20% gradient SDS-PAGE gel showing the purified Bst L.F. after factor Xa cleavage. Lane 1 shows approximately 4 ug of the final purified Bst Polymerase Large Fragment protein. Molecular weight markers in lane 8 are: 212, 158, 116, 97.2, 66.4, 55.6, 42.7, 36.5, 26.6, 20.0,14.3, and 6.5 kDa. The Bst Polymerase Large Fragment corresponds to approximately 67 kDa.

Figure 5:
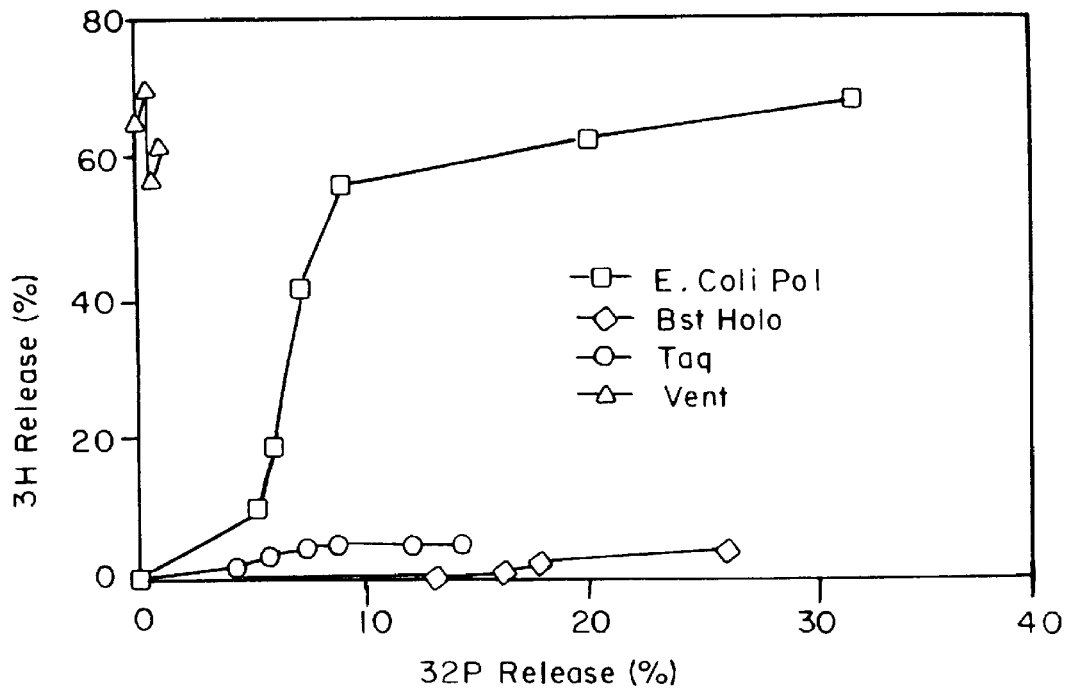

FIG. 5 is the result of an exonuclease activity assay to determine the directionality of Bst Pol I exonuclease. 5'-3' and 3'-5' exonuclease activities are determined using EcoRl digested pUC19, which is labeled on 3' ends with $^3$H and 5' ends with $^{32}$P. pUC19 is digested with EcoRl leaving 4 base 5' overhangs. $^3$H dTTP's are incorporated into the overhangs by Klenow fragment, thus labelling 3' ends with $^3$H. 5' ends are phosphorolated with $^{32}$P-gamma ATP by T4 Polynucleotide Kinase. The dual-labelled substrate is incubated separately with Bst DNA Polymerase 1, Vent DNA Polymerase and Taq DNA Polymerase at 65° C. and with E. Coli DNA Polymerase I at 37° C. for various amounts of time. DNA is precipitated out by the addition of 10% TCA and collected by centrifugation. Acid-soluable radioactivity present in the supernatant is quantified by liquid scintillation. Solubilization of $^3$H from 3' ends indicates the presence of 3'–5' exonuclease activity. Release of $^{32}$P from 5' ends indicates the presence of 5'–3' exonuclease activity. Bst DNA Polymerase (◇) does not remove $^3$H from 3' ends and is therefrore similar to Taq DNA Polymerase (0) because of its lack of 3'-5' exonuclease activity.

Figure 6:
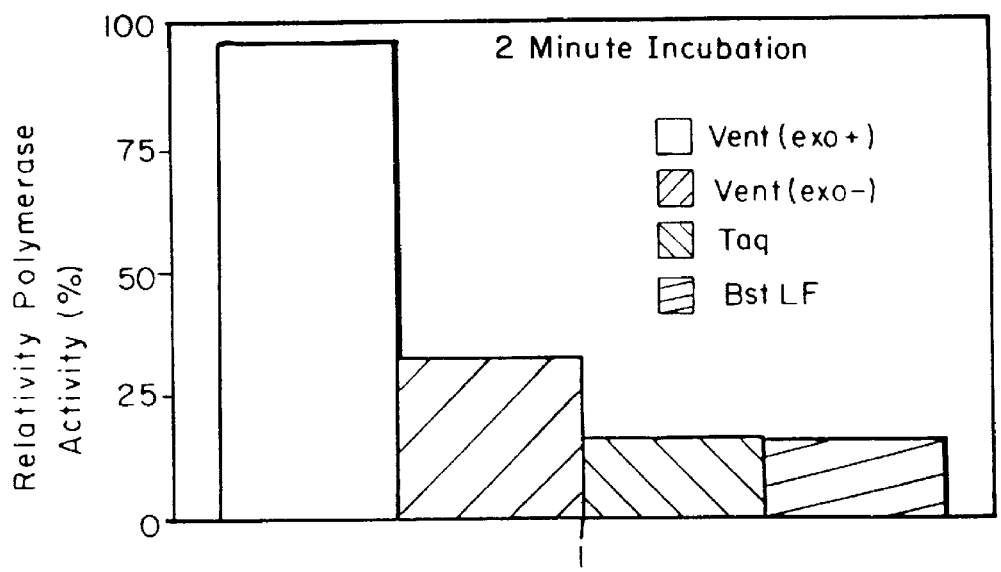

FIG. 6 is a proofreading exonuclease activity assay. M13mp18 single sdranded DNA was annealed with a primer containing a G:A mismatch at 3'-end. Vent DNA polymerase with 3' to 5' exonuclease can efficiently remove the mismatched G and then extend the primer, resulting a higher relative polymerase activity (FIG. 6, Vent exo$^+$). Taq polymerase does not have 3' to 5' exonuclease, therefore can not correct the mismatch, resulting a 5-fold lower relative polymerase activity (FIG. 5, Taq). Like Taq, Bst has a lower relative polymerase activity, indicating that it lacks the 3' to 5' exonuclease activity which is required for removing the mismatched G so that the 3' terminus can then be extended DNA polymerase.

DETAILED DESCRIPTION OF THE INVENTION

Figure 1:
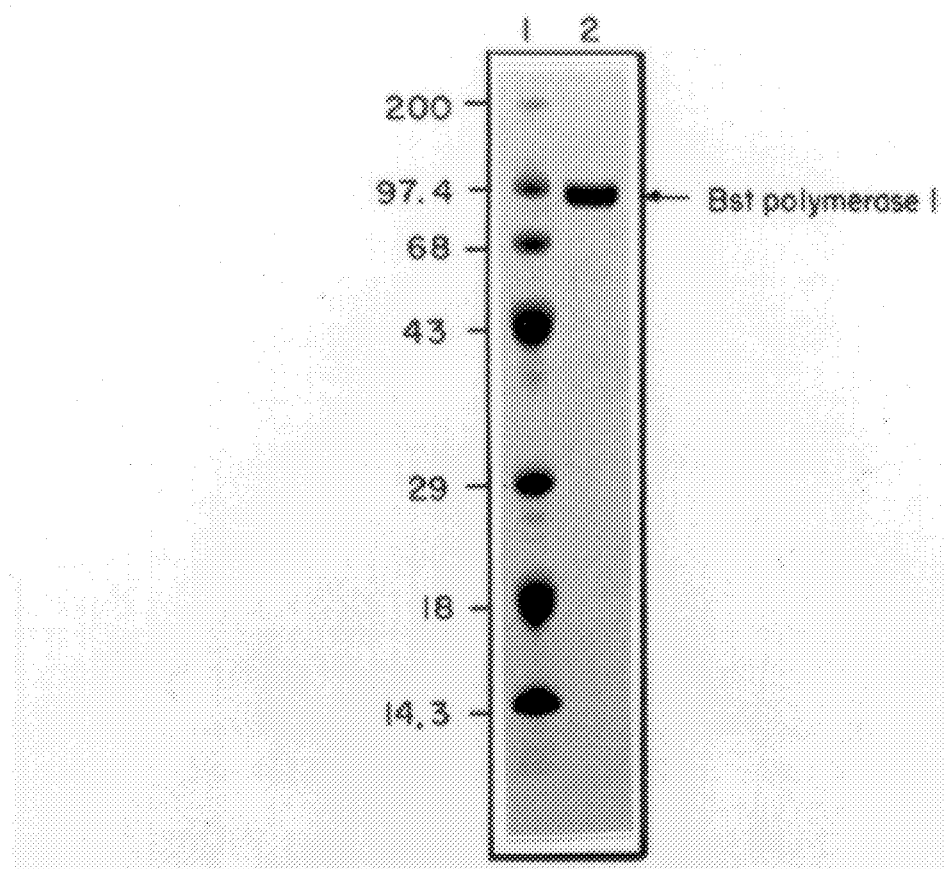
FIG. 1 is a 10–20% gradient SDS-PAGE gel showing the purified Bst DNA polymerase I along with molecular weight standard.

The preferred method described herein by which the large fragment of Bst Pol I is made includes the following steps:

1. Bst DNA polymerase I is purified from *Bacillus stearothermophilus*. This organism is a thermophilic bacterium, with a growth range between 45° C. and 70° C. After cell growth, Bst DNA polymerase I is purified using a multi-step process as follows: First, the cells are suspended in buffer A (20 mM KPO$_4$ buffer, pH 6.5; 1 mM EDTA; 10 mM beta-mercaptoethanol), sonicated and centrifuged. The KPO$_4$ concentration is adjusted to 200 mM in supernatant and the supernatant is then passed through a column which has a high affinity for nucleic acids such as DEAE Sepharose column. The nucleic acids present in the supernatant solution bind to the DEAE and thereby are separated from the proteins which pass through the column at 200 mM KPO$_4$ salt concentration. The flow through proteins are applied to a heparin sepharose column. The column is washed and the DNA polymerase enzyme activity eluted with a linear gradient such as 0 to 0.7 M KCl in buffer A. The peak DNA polymerase activity is dialyzed in buffer B (20 mM Tris-HCl, pH 7.4; 0.5 mM EDTA; 10 mM beta-mercaptoethanol) and applied to Q-sepharose column. The enzyme activity is eluted with a linear gradient such as 0.025 to 1M KCl in buffer B. Again, the peak DNA polymerase activity is dialyzed and applied to a heparin Tsk 1 column (Toso Haas). The enzyme is eluted with a linear gradient of 0.025 to 1M KCl in buffer B. The enzyme is about 95% pure at this stage (FIG. 1).

2. The Bst Pol I enzyme, prepared from step 1, is subjected to electrophoresis and electroblotted according to the procedure of Matsudaira, *J. Biol. Chem.* 262: 10035–10038 (1987), the disclosure of which is hereby incorporated by reference herein. The membrane is stained with Comassie Blue R-250 and the major protein band of 90 kDa is excised and subjected to sequential degradation according to the procedure of Waite-Rees et al, *J. Bacteriol.*, 173: 5207–5219 (1991), the disclosure of which is hereby incorporated by reference herein. The first 21 residues of the 90 kDa protein are Met-Lys-Lys-Lys-Leu-Val-Leu-lle-Asp-Gly-Asn-Ser-Val-Ala-Tyr-Arg-Ala-Phe-Phe-Ala-Leu (SEQ ID NO: 3). To clone and express Bst Pol I gene in E. coli, a degenerated primer (primer A) which contains a restriction enzyme (XbaI) cloning site and a ribosome binding site is made base on the amino acid sequence.

3. To determine the 3' end nucleotide sequence so that the Bst Pol I gene can be directly cloned by PCR, inverse PCR products are amplified from NgoMI and Sau3AI cleaved/self-ligated B. stearothermophilus genomic DNA template. The reaction which used NgoMI digested, self-ligated Bst DNA as a template yields a fragment approximately 0.95 kb in size. The reaction which used Sau3Al digested/self-ligated Bst DNA as a template yields a fragment approximately 1.5 kb in size. The two amplified DNA bands of 0.95 kb and 1.5 kb are excised from the agarose gel and subjected to DNA sequencing directly. A stop codon (TAA) was found 180 base pairs into the NgoMI digested/self-ligated sequence, and is thought to be the stop codon of the Bst DNA Polymerase I gene. Another primer (primer B) that anneals to the 3' end of the Bst Pol I gene and contains the NotI cloning site is made.

4. A PCR reaction is performed and a predicted 2.6 kb band is observed on agarose gel. The 2.6 kb fragment is purified from the gel and then digested with NotI and XbaI and cloned into NotI/XbaI digested pET-21a vector (Novagen, Madison, Wis.). The recombinant plasmid which contains Bst Pol I gene is transformed into ER2169 competent cells (New England Biolabs, Beverly, Mass.). A thermophilic DNA polymerase activity at 65° C. (about 30,000 u/gram host cell) is observed in mesophilic E. coli host, indicating the success on cloning and expressing Bst Pol I gene. The nucleotide sequence of the entire Bst Pol I gene is determined (FIG. 2) which corresponds to a 2631 bp uninterrupted open reading frame (ORF). The 2631-bp gene codes for a 876 amino acid. protein with calculated molecular weight of 99,007.67, which agrees with the observed molecular mass of about 97 kDa on 10 to 20% polyacrylamide gradient gel (FIG. 1).

5. It has been observed that digesting Bst DNA Polymerase I with the protease subtilisin results in the production of the Bst large fragment (Bst L.F.). Bst L.F. is a truncated polymerase that lacks the 5' to 3' exonuclease domain and is a very useful enzyme in DNA sequencing (Ye and Hong, *Scientia Sinica,* 30: 503–506 (1987), the disclosure of which is hereby incorporated by reference herein). Although subtilisin can be used to generate the Bst L.F., the efficiency is low due to the non-specific degradation of Bst polymerase by the subtilisin. In accordance with the present invention, it was discovered that making the Bst L.F. directly from the Bst Pol I gene with deletion at 5' end is more efficient than subtilisin digestion, which in turn, makes it more useful in applications such as DNA sequencing and strand displacement amplification, Walker et al., supra. The original experiment to clone and express Bst L.F., however, failed. It is possible that the mRNA being transcribed or the protein being translated from the truncated gene is unstable in vivo. It is also possible that the Bst large fragment is exceptionally lethal to the E. coli host and that only mutants with low, or no polymerase activity were being selected for. To overcome the problems, the 5' end truncated Bst Pol I gene was cloned into the pMAL-c2 vector in hopes of stabilizing the transcribed mRNA or of making the translated protein more stable or less lethal by creating an MBP-Bst L.F. fusion protein.

To define the N-terminal border of Bst L.F., purified Bst DNA polymerase I (FIG. 1) is digested with suitable amount of subtilisin and then the subtilisin-digested large fragment were subjected to electrophoresis on a Tris-Tricine 10 to 20% polyacrylamide gradient gel (Novex, San Diego, Calif.) and electroblotted (Matsudaira, *J. Biol. Chem,* 262: 10035–10038 (1987), the disclosure of which is hereby incorporated by reference herein). The protein band of approximately 67 KDa corresponding to the Bst L.F. was excised and subjected N-terminal protein sequencing (Waite-Rees et al., supra. The first 7 residues of the 67 KDa protein corresponds to Ala-Glu-Gly-Glu-Lys-Pro-Leu, (SEQ ID NO: 4) showing that the subtilisin cleavage site is between Ala 289 and Ala 290 (FIG. 2). The large fragment's N-terminal amino acid sequence matches the amino acid. sequence deduced from the cloned Bst Pol I gene (FIG. 2).

Figure 3:
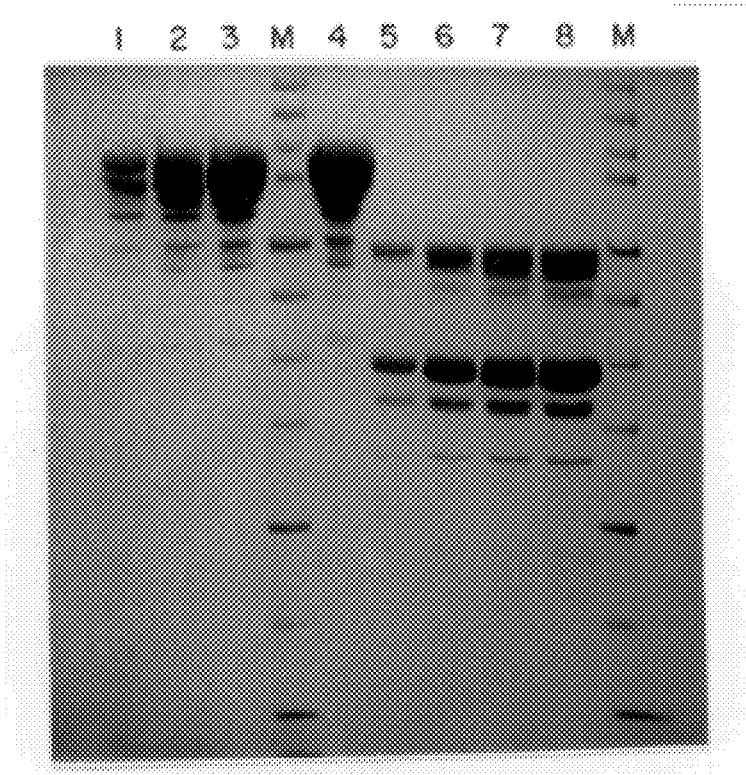
FIG. 3 is showing the cleavage of MBP-Bst L.F. fusion protein by Factor Xa. Lanes 1–4 show the uncleaved S-100 pool (approximately 2.7, 5.4, 10.7, and 21.4 ug, respectively). Lanes 5–8 show the same amounts of fusion protein cleaved with Factor Xa protease (1% mass ratio) at 4° C. for 18 hours.

Based on this sequence, a primer (primer C), containing FspI restriction enzyme site, is designed to anneal to the Bst Pol I gene at position 868 to 890 which corresponds to the beginning of Bst L.F. (FIG. 2). Another primer (primer D), with XbaI site, is designed to anneal to the 3' end of the gene. PCR is performed to amplify the 5' truncated Bst Pol I gene which encodes the Bst large fragment. A 1.8 kb DNA fragment is amplified, corresponding to the expected size of the Bst large fragment. The 1.8 kb fragment is cleaved by FspI(blunt end) and XbaI and then cloned into XmnI (blunt end) and XbaI cleaved pMAL-c2 Vector (New England Biolabs, Beverly, Mass.). The cloned gene is inserted directly downstream of the pMAL-c2 malE gene (from *E. coli*), which encodes for the maltose-binding protein (MBP), resulting in the expression of an MBP-Bst L.F. fusion protein (FIG. 3). The recombinant plasmid is transformed into *E. coli* RRI cells (New England Biolabs, Beverly, Mass.). Cells containing this plasmid are sonicated and centrifuged. Again, a thermophilic DNA polymerase activity at 65° C. (about 130,000 u/gram host cell) is observed in mesophilic *E. coli* host, indicating the MBP-Bst fusion is active at 65° C.

7. The supernatant from step 6 is applied to an amylose affinity column (detailed in example VI). The nucleic acids and all the other host cell proteins, except MBP-Bst fusion, pass through the column and thereby removed by washing the column with several column volumes of buffer C (200 mM NaCl; 20 mM Tris-HCl, pH 7.4; 1 mM EDTA; 1 mM DTT). The MBP-Bst L.F. fusion protein is eluted with 10 mM maltose in buffer C. The eluted fusion is further purified by a S-100 size exclusion column to eliminate any free MBP.

8. The purified MBP-Bst fusion protein can be cleaved by Factor Xa protease (New England Biolabs #800-10). After factor Xa cleavage, the 110 kDa MBP-Bst L.F. fusion was degraded and gave rise to the expected 67 kDa Bst L.F. and the 40 kDa MBP (FIG. 3). Both MBP-Bst L.F. fusion protein and the factor Xa cleaved Bst L.F. are active, but the factor Xa cleaved Bst L.F. (45,300 u/mg) has about 7-times higher specific activity the fusion (6,300 u/mg). The heat-denaturation of the mesophilic MBP in MBP-Bst fusion at 65° C. may be the reason of the low specific activity of the fusion. The cleaved Bst L.F. should be preferred enzyme for production because its thermostability and higher specific activity.

9. To remove the factor Xa and cleaved free MBP, the factor Xa digestion is heat-stressed by incubation at 65° C. for 20 minutes and then is applied to a Source-Q (Pharmacia Biotech) column which had been equilibrated to buffer E (50 mM NaCl; 20 mM Tris-HCl pH 7.8; 0.1 mM EDTA; 1 mM DTT). The enzyme is eluted with a linear gradient from 50 mM to 600 mM NaCl in buffer D. The Bst L.F. is diluted with seven volumes of buffer F (20 mM KPO4, pH 6.9; 0.1 mM EDTA; 1 mM DTT) and applied to a 1 cm×10 cm Heparin-TSK 5PW guard resin column which had been equilibrated to buffer G (50 mM NaCl, 20 mM KPO4, pH 6.9; 0.1 mM EDTA; 1 mM DTT). The enzyme is eluted with a linear gradient from 50 mM to 600 mM NaCl in buffer F. The enzyme-containing fractions are examined by SDS-PAGE and found to have the expected molecular weight of 67,000 and over 90% pure (FIG. 4). This recombinant Bst L.F. has a specific activity of 100,800 u/mg.

The recombinant Bst L.F., described here, is capable of doing strand displacement during replication and does not have either of the 5' to 3' and 3' to 5' exonuclease activity (FIG. 6), which differs from what is described in Epicentre's (Madison, Wis.) catalog presenting that Bst Pol I has a 3' to 5' exonuclease activity.

10. Exonuclease activity assays are carried out to determine the directionality of the exonuclease activity associated with our Bst DNA polymerase I. Linear PUC19 DNA substrate is prepared with 5'-$^{32}$P and 3'-$^{3}$H terminal labels and the solubilization of the two labels are monitored during incubation with Bst Polymerase I as well as Vent, E. coli Pol I and Taq DNA polymerases as contrals. Vent has a 3'-5' exonuclease and as a result, it solubilizes the $^{3}$H label. Taq has a 5'-3' exonuclease, therefore it solubilizes the $^{32}$P label.

E. coli Pol I has both 5'-3' and 3'-5' exonuclease, thus both $^{32}$P and $^{3}$H labels are solubilized during the incubation with E. coli Pol I. Like Taq, Only $^{32}$P label is solubilized by incubation with Bst Pol I, indicating it contains the 5'-3' exonuclease but lacks the 3'-5' exonuclease activity (FIG. 5). The sequence data showes that Bst Pol I does not have the "DXE" exo I motif in the 3'-5' exonuclease domain, which agreed with our exonuclease assay data.

To further confirm that Bst Pol I lacks the 3'-5' exonuclease activity, proofreading exonuclease assay is carried out using M13ssDNA annealed with a primer which contains a G:A mismatch at 3' end. Vent DNA polymerase with 3' to 5' exonuclease can efficiently remove the mismatched G and then extend the primer, resulting a higher relative polymerase activity (FIG. 6, Vent exo+). Taq polymerase does not have 3' to 5' exonuclease, therefore can not correct the mismatch, resulting a 5-fold lower relative polymerase activity (FIG. 6, Taq). Like Taq, Bst has a lower relative polymerase activity, indicating that it lacks the 3' to 5' exonuclease activity which is required for removing the mismatched G so that the 3' terminus can then be extended DNA polymerase.

The following examples are given to illustrate embodiments of the present invention as it is presently preferred to practice. It will be understood that this example is illustrative, and that the invention is not to be considered as restricted thereto except as indicated in the appended claims.

EXAMPLE I

CLONING OF B. stearothermophilus DNA POLYMERASE I

GENE

1. Determination Of The Bst Pol I Gene's 3'-End Using Inverse PCR

Restriction digests were performed in separate tubes using 1.2 μg of B. stearothermophilus genomic DNA per reaction. 50 U of Sau3AI (New England Biolabs, #169) was added to a mix which contained the DNA in 45 μl of NEBuffer Sau3AI (New England Biolabs NEBuffer Sau3AI=100 mM NaCl, 10 mM Bis Tris Propane-HCl, 10 mM MgCl$_2$, 1 mM dithiothreitol, pH 7.0 @ 25° C.). 50 U of NgoMI (New England Biolabs, #564) was added to a mix which contained the DNA in 45 μl of NEBuffer 4 (New England Biolabs NEBuffer 4=50 mM potassium acetate, 20 mM Tris-acetate, 10 mM magnesium acetate, 1 mM dithiotheitol, pH 7.9 @ 25° C.). The Sau3AI reaction contained 100 μg/ml BSA. The final volume for both reactions were 50 μl. Both digests were incubated for one hour at 37° C. Restriction enzyme was removed from the digests by extraction with phenol (once) and chloroform (twice). The DNA was precipitated by adding 5 μl of 3 M sodium acetate and 100 μl of 95% ethanol/5% isopropanol to each digest and collected by centrifugation. The DNA was resuspended in separate tubes in 500 μl of T4 DNA Ligase Buffer (New England Biolabs T4 DNA Ligase Buffer=50 mM Tris-HCl pH 7.8, 10 mM MgCl$_2$, 10 mM dithiothreitol, 1 mM ATP, 25 μg/μl BSA) and 3,000 U of T4 DNA Ligase (New England Biolabs, #202) was added. Both ligations were incubated overnight at 16° C. followed by 72° C. for 20 minutes.

The self-ligated Bst genomic DNA was then used as the templates in inverse PCR reactions aimed at locating the 3' end of the DNA polymerase gene. PCR reactions were performed in separate tubes using 10 ng of each digested and self-ligated DNA, 200 μM dNTPs, 50 ng of the forward primer (5'GATTTAGCGGCACGGCT GAAAGAA3' (SEQ ID NO: 5) and 50 ng of the reverse primer (5'CTGCAAAACTGCGGAC GTTGA3' (SEQ ID NO: 6) in 49.5 μl of ThermoPol Buffer (New England Biolabs ThermoPol Buffer=10 mM KCl, 20 mM Tris-HCl pH 8.8 @ 25° C., 10 mM (NH$_4$)$_2$SO$_4$, 2 mM MgSO$_4$, 0.1% Triton X-100). The forward and reverse primers anneal to Bst genomic DNA 55 base pairs away from each other and are designed to extend DNA in opposite directions.

The DNA sequence which the primers were designed from came from a 642 base pair fragment of the Bst DNA polymerase I gene which had previously been cloned into the pGEM-T vector (Promega, #A362A (Promega, Madison, Wis.)) and sequenced (Sanger, et al., PNAS, 74: 5463–5467 (1977), the disclosure of which is hereby incorporated by reference herein). 2.5 U of Taq DNA Polymerase (Perkin Elmer, N801-0046 (Perkin Elmer, Branchburg, N.J.)) were added to each reaction bringing the final volume up to 50 μl. Four additional PCR reactions were also performed, using 10 ng of each template in the same reaction mixture that was just described. However, for these reactions, each of the two primers was incubated separately with the two DNA templates (4 reactions). Products of these reactions would represent background created by the same primer annealing in two locations and amplifying the region in between.

The initial segment for all PCR reactions consisted of one cycle for 2 minutes at 94° C. The segments of each subsequent PCR cycle were the following: 0.5 minutes at 94° C., 1 min at 62° C. and 2 minutes at 72° C. for 20 cycles and 0.5 minutes at 94° C., 1 minute at 62° C. and 4 minutes at 72° C. for 10 cycles. The last segment consisted of one cycle for 2 minutes at 72° C. and 10 minutes at 25° C. 20 μl of each 50 μl reaction were removed and subjected to agarose gel electrophoresis with ethidium bromide present in order to determine if amplification had occurred. The reaction which used Sau3Al digested, self-ligated Bst DNA as a template yielded an amplified fragment of approximately 1.5 kb in size. The reaction which used NgoMl digested, self-ligated Bst DNA as a template yielded an amplified fragment of approximately 0.95 kb in size. The two fragments did not correspond to any fragment created in the 4 background reactions.

The PCR reactions, using both the forward and reverse primers to amplify both templates separately, were repeated. The same PCR conditions were used as before, but each reaction was carried out in 8 separate tubes using identical reagents in a 50 μl reaction volume. All 400 μl of each reaction was subjected to agarose gel electrophoresis on a 1% low temperature melting agarose gel in TAE buffer (40 mM Tris-acetate; 1 mM EDTA) with ethidium bromide present. The appropriate bands (1.5 kb for Sau3Al and 0.95 for NgoMl) were excised and heated to 65° C. in separate tubes. After the agarose was melted, 50 μl of β-Agarose I buffer was added (New England Biolabs β-Agarose I buffer=10 mM Bis Tris-HCl, pH 6.5, 1 mM Na₂EDTA) and the tubes were cooled to 40° C. 4 U of β-Agarose I were added to each reaction (New England Biolabs, #392). β-Agarose I treatment was for one hour at 40° C. The β-Agarose and DNA polymerase were removed by extraction with phenol (once) and chloroform (twice). DNA was precipitated by adding 50 μl of 3M sodium acetate and 1000 μl of 95% ethanol/5% isopropanol and collected by centrifugation. Each DNA pellet was resuspended in 50 μl 1XTE (10 mM Tris-HCl, pH 8.0, 1 mM EDTA) and 1 μl samples were subjected to agarose gel electrophoresis in order to determine DNA concentration. Both DNA fragments were sequenced (Sanger, et al., *PNAS*, 74: 5463–5467 (1977), the disclosure of which is hereby incorporated by reference herein) using the forward primer, which was expected to extend DNA towards the 3' end of the polymerase gene. A stop codon (TAA) was found 180 base pairs into the NgoMl digested, self-ligated sequence.

2. Amplification Of Bst Pol I Gene

2 μg of Bst DNA Polymerase I were subjected to electrophoresis on a Tris-Tricine 10 to 20% polyacrylamide gradient gel (Novex, San Diego, Calif.) and electroblotted (Matsudaira, *Biol. Chem*, 262: 10035–10038 (1987), the disclosure of which is hereby incorporated by reference herein). The membrane was stained with Comassie blue R-250 and the protein band of approximately 97 KDa was excised and subjected to sequential degradation (Waite-Rees et al, *J. Bacteriol.*, 173: 5207–5219 (1992), the disclosure of which is hereby incorporated by reference herein). The first 7 residues of the 97 kDa protein corresponded to Met-Lys-Lsy-Lys-Leu-Val-Leu (SEQ ID NO: 7). Primers were designed based on the N-terminal amino acid. sequence of Bst DNA Polymerase I (5'WTGAARAARAARCTNGT NYT 3' (SEQ ID NO: 8)) and the sequence of the 3' end of the gene obtained from inverse PCR (5'TCTTATTTNGCATCATACCATGT 3' (SEQ ID NO: 9)). 150 ng of Bst genomic DNA, 100 pmoles of each primer and 200 μM dNTPs were added to 98 μl of ThermoPol Buffer. One μl (5 U) of Taq DNA polymerase and i μl (0.05 U) of Deep Vent DNA polymerase (New England Biolabs, #258) were added to initiate the PCR reaction (94° C. 0.5 min., 45° C. 1 min., 72° C. 3 min., 35 cycles). 15 μl were removed and subjected to agarose gel electrophoresis with ethidium bromide present. A 2.6 kb fragment was amplified, corresponding to the expected size of the Bst DNA Polymerase I gene. The remaining 85 μl were subjected to gel electrophoresis on a 1% low temperature melting agarose gel in TAE buffer with ethidium bromide and the 2.6 kb fragment was excised. The slice containing the DNA was treated with β-Agarose I, extracted with phenol and chloroform and precipitated with ethanol and sodium acetate all as described before. The DNA pellet was resuspended in TE buffer. Restriction mapping of the 2.6 kb fragment was performed to determine the presence of unique restriction sites so that primers could be designed with these sites, allowing the entire fragment to be cloned into a vector. Ncol, Notl and Xbal did not cut the DNA fragment so two primers were designed, the first annealing to the 3' end of the fragment and containing Ncol and Notl sites (5'TCCATGGCGGCCGCTCTTATTTN GCATCATACCATGT3' (SEQ ID NO: 10) and the second annealing to the 5' end of the fragment, containing an Xbal site (5'ATTCTAGAGGAAA CAGACCWTGAARAARA-ARCTNGTNYT3' (SEQ ID NO: 11)). A PCR reaction was performed, using the exact conditions used to amplify the 2.6 kb fragment but substituting the original primers with those containing the restriction enzyme sites. 6 identical tubes containing a total of 600 μl PCR reaction mixture were used.

All 600 μl were subjected to gel electrophoresis on a 1% low temperature melting agarose gel and the 2.6 kb amplified DNA fragment excised from the gel. The agarose-embedded DNA was dialyzed against 1 ml of NEBuffer 2 (New England Biolabs NEBuffer 2=10 mM Tris-HCl, 10 mM MgCl₂, 50 mM NaCl, 1 mM DTT, pH 7.9 @ 25° C.) for 45 minutes at 4° C. The agarose was then placed in a new tube and melted at 65° C. for 10 min. The molten agarose was cooled to 37° C. and 7 μl of 10 mg/ml BSA, 3.5 U β-Agarose I (New England Biolabs, Beverly, Mass.) and 100 U of Xbal (New England Biolabs, Beverly, Mass.) were added. After 1 hour incubation at 37° C., 5M NaCl and 1M Tris, pH 8.0 were added so that the final concentrations of 100 mM and 50 mM respectively. 100 U of Notl (New England Biolabs, Beverly, Mass.) were then added to the Xbal digestion and incubated at 37° C. for one more hour. 1 μg of pET-21a (Novagen, Madison, Wis.), which contains a T7 promoter, was digested in 45 μl of NEBuffer 2 (New England Biolabs, Beverly, Mass.) with 25 U of Notl and 50 U of Xbal at 37° C. for 1 hour. The reactions were extracted with phenol and chloroform, precipitated with sodium acetate and ethanol, as described before, and resuspended in 60 μl 1XTE. 400 ng of Xbal/Notl digested PCR product were ligated to 100 ng of Xbal/Notl digested pET-21a in 45 μl T4 DNA Ligase buffer. 5,000 U of T 4 DNA Ligase were added, to make the final volume 50 μl, and the reaction was incubated at 16° C. for 4 hours.

100 μl of CaCl competent (Maniatis, et al., *Molecular Cloning: A Laboratory Manual* (1982), the disclosure of which is hereby incorporated by reference herein) RRI cells (New England Biolabs) were transformed with 10 1 of ligation mix and incubated overnight on LB (Lauria Broth, 1 Liter: 10 g tryptone, 5 g yeast extract, 170 mM NaCl, 0.5 mM glucose, 0.5 mM MgCl₂, pH 7.2) plates with ampicillin (100 μg/ml) at 37° C. Colonies were picked and mini-plasmid preparations (Wizard Minipreps, DNA purification system, Promega, Madison, Wis.) screened for a 2.6 kb insert. 5 out of the 38 transformants screened contained the correct insert and 1 μl of mini-prep DNA from one of the transformants with the correct insert was used to transform 50 μl of CaCl competent ER2169 cells (New England Biolabs, Beverly, Mass.), which are capable of T7 RNA polymerase production upon induction with IPTG. The cells were spread on an LB plate with ampicillin (100 μg/ml) and incubated overnight at 37° C. One colony was picked and grown at 37° C. in 20 ml of LB with ampicillin (100 μg/ml) until a reading of Klett 200 was obtained. IPTG was added to a final concentration of 0.5 mM and the cells were grown for an additional 2 hours at 37° C. The cells were harvested by centrifugation, resuspended in 10 ml of sonication buffer (50 mM NaCl, 10 mM Tris pH 7.4, 0.1 mM EDTA, 1 mM 2-mercaptoethanol) and lysed by sonication. The lysate was separated by centrifugation and incubated at 65° C. for 20 minutes to denature any DNA polymerase contributed by the E. coli host cells. Denatured protein was pelleted by centrifugation and the supernatant was assayed for Bst DNA Polymerase I activity by quantifying the incorporation of $^3$H dTTP in primed M13mp18 (New England Biolabs, Beverly, Mass.) single stranded DNA. 5 μl of the supernatant were incubated at 65° C. for 5 minutes with 45 μl of Bst polymerase assay mix, which included 2.86 mM M13 single stranded DNA with primer #1224 (New England Biolabs, Beverly, Mass.) annealed to it, 200 μM dATP, dCTP, dGTP, 100 μM $^3$H dTTP, 100 μg/ml BSA, 20 mM Tris pH 8.8, 50 mM KCl and 10 mM $MgCl_2$. 40 μl of the reaction were spotted onto filter paper (Whatman, 024–1030) and the filter paper was washed 3 times with 10% trichloroacetic acid and once with 100% isopropanol. The filter was dried and incorporation of $^3$H dTTP was quantified by liquid scintillation counting. It was determined that one gram of induced ER2169 cells produced approximately 30,000 U of Bst DNA polymerase I.

EXAMPLE II

CLONING OF 5'-END TRUNCATED BST POL I GENE WHICH ENCODES THE BST LARGE FRAGMENT

1. Define The N-terminal Border Of Bst L.F. With Subtilisin

50 μg of Bst DNA Polymerase I were digested with subtilisin (75 ng/μl final concentration) at room temperature for 5 minutes in the presence of 140 mM $K_2PO_4$, 3 mM β-mercaptoethanol, 30 mM ammonium sulfate and 125 μg calf thymus DNA. The digestion was stopped by the addition of phenylmethylsulfonyl fluoride at a final concentration of 2.4 mg/ml. The subtilisin-digested Bst L.F. produced was quantified by electrophoresis on a 4–20% SDS-PAGE gradient gel (Daiichi Integrated Separation Systems, Natick, Mass.). 2 μg of the subtilisin-digested Bst polymerase I was subjected to electrophoresis on a Tris-Tricine 10 to 20% polyacrylamide gradient gel (Novex, San Diego, Calif.) and electroblotted (Matsudaira, J. Biol. Chem, 262: 10035–10038 (1987), the disclosure of which is hereby incorporated by reference herein). The N-terminal amino acid sequence of this 67 kDa large fragment was determined as described before. The first 7 residues of the 67 KDa protein corresponded to Ala-Glu-Gly-Glu-Lys-Pro-Leu (SEQ ID NO: 12), indicating the N-terminal border of Bst L.F. is between Ala289 and Ala290 (FIG. 2). Based on this information, a primer was designed (5'AATTTGCGCAG AAGGGGAGAAACCGCTTGA3' (SEQ ID NO:14)) to anneal to the downstream of the border of the Bst L.F. The primer was designed with an FspI cleavage site so that it could be digested with FspI and ligated into the XmnI site of the pMAL-c2 vector. Another primer, with an XbaI cleavage site, was designed (5'TATTCTAG ATCTTATTTGGCAT-CATAC CATGT3' (SEQ ID NO:14)) to anneal to the 3' end of Bst Pol I gene.

PCR was performed to amplify the Bst large fragment gene. 1.6 μg of Bst genomic DNA were added to 392 μl of ThermoPol Buffer plus 400 ng of each primer and 200 μM dNTPs. 40 U of Taq DNA polymerase (Perkin Elmer, Branchburg, N.J.) and 0.4 U Deep Vent DNA Polymerase (New England Biolabs, Beverly, Mass.) were added to the reaction. PCR was carried out as following: 94° C. 0.5 min., 50° C. 1 min., 72° C. 3 min. for 18 cycles. A 1.8 kb fragment was amplified, corresponding to the expected size of the Bst DNA large fragment gene. The remaining PCR product was purified and cleaved with FspI and XbaI. 195 ng of the FspI/XbaI digested PCR product were ligated to 75 ng of the XmnI/XbaI digested pMAL-c2 in 45 μl T4 DNA Ligase buffer (New England Biolabs, Beverly, Mass.). 5,000 U of T4 DNA Ligase were added and the reaction was incubated at 16° C. for 4 hours. 100 μl of CaCl competent (Maniatis, et al., Molecular Cloning: A Laboratory Manual (1982), the disclosure of which is hereby incorporated by reference herein) RRI cells (New England Biolabs, Beverly, Mass.) were transformed with 10 μl of ligation mixture and incubated overnight on LB plates with ampicillin (100 μg/ml) at 37° C. Correct insert was screened through mini-plasmid preparations. 2 out of the 16 transformants screened contained the 1.8 kb expected insert. The cloned gene was inserted directly downstream of the pMAL-c2 malE gene (from E. coli), which encodes for the maltose-binding protein (MBP), resulting in the expression of an MBP-Bst L.F. fusion protein upon induction with IPTG. The recombinant plasmid with the right construct was used to transform 50 μl of CaCl competent TB1 cells (New England Biolabs, Beverly, Mass.). 20 ml of LB with ampicillin (100 μg/ml) was inoculated with a single colony from the transformation plate. IPTG was added to 0.5 mM when the culture reached Klett 200 and the cells were grown for an additional 2 hours at 37° C.

The cells were harvested by centrifugation, resuspended in 10 ml of sonication buffer and lysed by sonication. The lysate was separated by centrifugation and incubated at 65° C. for 20 minutes to denature any DNA polymerase contributed by the host cells. Denatured protein was pelleted by centrifugation and the supernatant was assayed for Bst polymerase activity as described in example I. It was determined that one gram of transformed TB1 cells produced approximately 130,000 U of Bst large fragment. A sample of the fusion construct containing BstI L.F. has been deposited under the Budapest Treaty at the Americant Type Culture Collection on Aug. 2, 1995 and received ATCC Accession Number 69877.

EXAMPLE III

PURIFICATION OF BST DNA POLYMERASE LARGE FRAGMENT

All steps were performed at 4 C, except Step 5.

Step 1: Preparation of crude extract.

64 grams of the enzyme bearing cells (NEB #956) were thawed and resuspended in buffer C (200 mM NaCl; 20 mM Tris-HCl, pH 7.4; 1 mM EDTA; 1 mM DTT). The cells were ruptured by sonicating for 8 minutes. The extract was centrifuged in a Beckman J2-21 centrifuge at 4 C at 12,000 rpm for 30 minutes. The supernatant fluid was decanted.

Step 2: Amylose Affinity Chromatography.

The supernatant fluid from step 1 was applied to a 200 ml Amylose (NEB #800-21) column which had been equilibrated with buffer C. The column was washed with 2200 ml of buffer C, and the enzyme was eluted with 800 ml buffer C containing 10 mM maltose. The protein peak fractions were pooled and concentrated by dialysis into buffer D (500 mM NaCl; 20 mM Tris-HCl, pH 7.4; 0.1 mM EDTA; 1 mM DTT; 50% Glycerol).

Step 3: S-100 Size Exclusion Chromatography.

The pool from the previous step was applied to a 5 cm×90 cm S-100 (Pharmacia Biotech., Piscataway, N.J.) column which had been equilibrated in buffer D. The enzyme was eluted by applying 2,000 ml of S buffer. The enzyme-containing fractions were determined by SDS-PAGE and were pooled and dialyzed into buffer E (50 mM NaCl; 20 mM Tris-HCl pH 7.8; 0.1 mM EDTA; 1 mM DTT).

Step 4: Cleavage of the fusion protein by Factor Xa protease.

200 mg of enzyme from the previous step (in 150 ml) were incubated with 2 mg of Factor Xa (New England Biolabs #800-10) for 22 hours at 4° C.

Step 5: Heat-stressing of Factor Xa.

The 150 ml cleavage product from step 4 was then heat-stressed by incubation at 65° C. for 20 minutes, followed by chilling to 4° C.

Step 6: Source-Q Ion-Exchange Chromatography.

The pool from the previous step was applied to a 1.6 cm×10 cm Source-Q (Pharmacia Biotech., Piscataway, N.J.) column which had been equilibrated to buffer E. The enzyme was eluted with a 150 ml linear gradient from 50 mM to 600 mM NaCl in the same buffer. The enzyme-containing fractions were determined by SDS-PAGE and were pooled.

Step 7: Heparin-TSK 5PW Guard Resin Column Chromatography.

The pool from the previous step was diluted with seven volumes of 20 mM KPO4 (pH 6.9), 0.1 mM EDTA, 1 mM DTT and applied to a 1 cm×10 cm Heparin-TSK 5PW guard resin column which had been equilibrated to buffer G (50 mM NaCl, 20 mM KPO4, pH 6.9; 0.1 mM EDTA; 1 mM DTT). The enzyme was eluted with a 100 ml linear gradient from 50 mM to 600 mM NaCl in H buffer. The enzyme-containing fractions were determined by SDS-PAGE (FIG. 4) and were pooled and dialyzed against 20 volumes of storage buffer (50 mM KCl, 10 mM Tris-HCl (pH 7.5), 0.1 mM EDTA, 1 mM DTT). The enzyme preparation was substantially pure and free from other contaminating enzymes/proteins and contained no detectable exonuclease activities as determined by incubating 1,000 units in a 50 ul reaction in optimal reaction conditions for 4 hours.

---

What is claimed is:

1. Isolated DNA coding for *Bacillus stearothermophilus* DNA polymerase I, of SEQ ID NO: 2, wherein the expression product of said isolated DNA is substantially free of 3' to 5' exonuclease.

2. The isolated DNA of claim 1, wherein the expression product of said isolated DNA polymerase is substantially free of 5' to 3' exonuclease.

3. The isolated DNA of claim 1, wherein the isolated DNA comprises nucleotides 868 to 2631 of SEQ ID NO: 1.

4. A vector comprising the isolated DNA of claim 1, 2 or 3.

5. A host cell transformed by the vecor of claim 4.

6. Substantially pure recombinant *Bacillus stearothermophilus* DNA polymerase I, of SEQ ID NO: 2, wherein said polymerase is substantially free of 3' to 5' exonucleases.

7. The polymerase of claim 6, wherein the polymerase is substantially free of 5' to 3' exonuclease.

8. A fusion protein comprising the recombinant polymerase of claim 6 or 7 fused to a fusion partner.

9. The fusion protein of claim 8, wherein the fusion partner comprises a sugar-binding protein.

10. The fusion protein of claim 9, wherein the sugar-binding protein comprises maltose binding protein.

11. A method for producing a recombinant *Bacillus stearothermophilus* DNA polymerase I, SER ID NO: 2, comprising:

(a) isolating DNA which codes for a said *Bacillus stearothermophilus* DNA polymerase I;

(b) fusing the isolated DNA of step (a) to a DNA fusion partner;

(c) inserting the DNA of step (b) into a cloning vector;

(d) transforming a host cell with the vector of step (c);

(e) culturing the host cell of step (d) under conditions suitable for expression; and (f) recovering a hybrid polypeptide the BstI DNA polymerase fused to the expression product of the DNA coding for the fusion partner.

12. The method of claim 11, wherein the recombinant polymerase is substantially free of 3' to 5' exonuclease activity.

13. The method of claim 12, wherein the recombinant polymerase is substantially free of 5' to 3' exonuclease activity.

14. The method of claim 11, wherein the fusion partner comprises a sugar-binding protein.

15. The method of claim 14, wherein the sugar-binding protein comprises maltose binding protein.

* * * * *

UNITED STATES PATENT AND TRADEMARK OFFICE
CERTIFICATE OF CORRECTION

PATENT NO. : 5,814,506

DATED : September 29, 1998

INVENTOR(S) : Kong, et al.

Page 1 of 3

It is certified that error appears in the above-identified patent and that said Letters Patent is hereby corrected as shown below:

Column 2, line 49, replace "gene" with --Gene--

Column 2, line 55, replace "Enzumol." with --Enzymol.--

Column 2, line 58, replace "approach, The" with --approach, the--

Column 3, line 66, replace "phosphorolated" with --phosphorylated--

Column 4, line 2, replace "Coli" with --coli--

Column 4, line 11, replace "therefrore" with --therefore--

UNITED STATES PATENT AND TRADEMARK OFFICE
CERTIFICATE OF CORRECTION

PATENT NO. : 5,814,506
DATED : September 29, 1998
INVENTOR(S) : Kong et al

It is certified that error appears in the above-identified patent and that said Letters Patent is hereby corrected as shown below:

Column 4, line 14, replace "sdranded" with --stranded--

Column 7, line 13, replace "KPO4" with --$KPO_4$--

Column 7, line 16, replace "KPO4" with --$KPO_4$--

Column 7, line 33, replace "PUC19" with --pUC19--

Column 7, line 37, replace "contrals" with --controls--

Column 7, line 45, replace "showes" with --shows--

Column 9, line 8, replace "Sau3A1" with --Sau3AI--

Column 9, line 57, replace "Lsy" with --Lys--

UNITED STATES PATENT AND TRADEMARK OFFICE
CERTIFICATE OF CORRECTION

PATENT NO. : 5,814,506
DATED : September 29, 1998
INVENTOR(S) : Kong, et al.

It is certified that error appears in the above-identified patent and that said Letters Patent is hereby corrected as shown below:

Column 9, line 65, replace "i µl" with --1 µl--

Column 12, line 9, replace "following" with --follows--

Column 14, line 12, replace "KPO4" with --KPO$_4$--

Column 14, line 15, replace "KPO4" with --KPO$_4$--

Signed and Sealed this

Second Day of March, 1999

Attest:

Q. TODD DICKINSON

Attesting Officer

Acting Commissioner of Patents and Trademarks

UNITED STATES PATENT AND TRADEMARK OFFICE

CERTIFICATE OF CORRECTION

PATENT NO.: 5,814,506

DATED: September 29, 1998

INVENTOR(S): Kong, et al.

It is certified that errors appear in the above-identified patent and that said Letters Patent is hereby corrected as shown below:

Column 3, line 8, replace "pET21 a" with --pET21a--

Column 3, line 13, replace "polymerase 1" with --Polymerase I--

Column 3, line 61, replace "EcoR1" with --EcoRI--

Column 3, line 63, replace "EcoR1" with --EcoRI--

Column 5, line 7, replace "Xba1" with --XbaI--

Column 5, line 12, replace "NgoM1" with --NgoMI--

Column 5, line 12, replace "Sau3A1" with --Sau3AI--

Column 5, line 14, replace "NgoM1" with --NgoMI--

Column 5, line 17, replace "Sau3A1" with --Sau3AI--

Column 5, line 22, replace "NgoM1" with --NgoMI--

Column 5, line 26, replace "Not1" with -- NotI--

Column 5, lines 29-30, replace "Not1 and Xba1" with --NotI and XbaI--

Column 5, line 30, replace "Not1/Xba1" with --NotI/XbaI--

Column 6, line 28, replace "Xba1" with --XbaI--

Column 6, line 33, replace "Fsp1" with --FspI--

Column 6, line 33, replace "Xba1" with --XbaI--

UNITED STATES PATENT AND TRADEMARK OFFICE

CERTIFICATE OF CORRECTION

PATENT NO.: 5,814,506

Page 2 of 4

DATED: September 29, 1998

INVENTOR(S): Kong, et al.

It is certified that errors appear in the above-identified patent and that said Letters Patent is hereby corrected as shown below:

Column 6, line 33, replace "Xmn1" with --XmnI--

Column 6, line 34, replace "Xba1" with --XbaI--

Column 8, line 11, replace "Sau3A1" with --Sau3AI--

Column 8, line 13, replace "Sau3A1" with --Sau3AI--

Column 8, line 13, replace "Sau3A1" with --Sau3AI--

Column 8, line 15, replace "NgoM1" with --NgoMI--

Column 8, line 20, replace "Sau3A1" with --Sau3AI--

Column 9, line 10, replace "NgoM1" with --NgoMI--

Column 9, line 23, replace "Sau3A1" with --Sau3AI--

Column 9, line 24, replace "NgoM1" with --NgoMI--

Column 9, line 35, replace "1XTE" with --1X TE--

Column 9, line 44, replace "NgoM1" with --NgoMI--

Column 12, line 13, replace "Fsp1 and Xba1" with --FspI and XbaI--

Column 10, line 15, replace "Nco1, Not1 and Xba1" With --NcoI, NotI and XbaI--

Column 10, line 17, replace "Nco1" with --NcoI--

Column 10, line 18, replace "Not1" with --NotI--

UNITED STATES PATENT AND TRADEMARK OFFICE
CERTIFICATE OF CORRECTION

PATENT NO. : 5,814,506
DATED : September 29, 1998
INVENTOR(S) : Kong, et al.

It is certified that error appears in the above-identified patent and that said Letters Patent is hereby corrected as shown below:

Column 10, line 20, replace "Xba1" with --XbaI--

Column 10, line 38, replace "Xba1" with --XbaI--

Column 10, line 41, replace "Not1" with --NotI--

Column 10, line 43, replace "Xba1" with --XbaI--

Column 10, line 46, replace "Not1" with --NotI--

Column 10, line 47, replace "Xba1" with --XbaI--

Column 10, line 50, replace "Xba1/Not1" with --XbaI/NotI--

Column 10, line 51, replace "Xba1/Not1" with --XbaI/NotI--

Column 10, line 58, replace "10 1" with --10 µl--

Column 11, line 62, replace "NO:14" with --NO:13--

Column 11, line 64, replace "Fsp1" with --FspI--

Column 11, line 65, replace "Fsp1" with --FspI--

UNITED STATES PATENT AND TRADEMARK OFFICE

CERTIFICATE OF CORRECTION

PATENT NO.:    5,814,506

DATED:         September 29, 1998

INVENTOR(S):   Kong, et al.

It is certified that errors appear in the above-identified patent and that said Letters Patent is hereby corrected as shown below:

Column 11, line 65, replace "Xmn1" with --XmnI--

Column 11, line 66, replace "Xba1" with --XbaI--

Column 12, line 14, replace "Fsp1/Xba1" with
    --FspI/XbaI--

Column 12, line 15, replace "Xmn1/Xba1" with
    --XmnI/XbaI

Signed and Sealed this

Sixth Day of April, 1999

Attest:

Q. TODD DICKINSON

Attesting Officer    Acting Commissioner of Patents and Trademarks